United States Patent
Huang et al.

(10) Patent No.: US 12,372,672 B2
(45) Date of Patent: Jul. 29, 2025

(54) MEMBRANE-PEROVSKITE FILMS, DEVICES, AND METHODS OF PREPARATION

(71) Applicant: The University of North Carolina at Chapel Hill, Chapel Hill, NC (US)

(72) Inventors: Jinsong Huang, Chapel Hill, NC (US); Jingjing Zhao, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 28 days.

(21) Appl. No.: 17/769,067

(22) PCT Filed: Oct. 16, 2020

(86) PCT No.: PCT/US2020/056140
§ 371 (c)(1),
(2) Date: Apr. 14, 2022

(87) PCT Pub. No.: WO2021/077006
PCT Pub. Date: Apr. 22, 2021

(65) Prior Publication Data
US 2024/0111066 A1  Apr. 4, 2024

Related U.S. Application Data

(60) Provisional application No. 62/923,037, filed on Oct. 18, 2019.

(51) Int. Cl.
*G01T 1/24* (2006.01)
*G01T 1/161* (2006.01)
*G01T 1/202* (2006.01)

(52) U.S. Cl.
CPC ............... *G01T 1/24* (2013.01); *G01T 1/161* (2013.01); *G01T 1/2023* (2013.01)

(58) Field of Classification Search
CPC ......... G01T 1/24; G01T 1/161; G01T 1/2023; C04B 2235/768; C04B 35/56; B32B 9/06;
(Continued)

(56) References Cited

U.S. PATENT DOCUMENTS

2004/0238750 A1  12/2004 Vafi et al.
2009/0321651 A1  12/2009 Lu et al.
(Continued)

FOREIGN PATENT DOCUMENTS

EP       0129109 A1   12/1984
KR    101003693 B1 *  12/2010 ............... G01T 1/00

OTHER PUBLICATIONS

Tan, Qishuo, et al. "Vacuum-filtration enabled large-area CsPbBr 3 films on porous substrates for flexible photodetectors." Journal of Materials Chemistry C 7.43 (2019): 13402-13409. (Year: 2019).*
(Continued)

*Primary Examiner* — Edwin C Gunberg
*Assistant Examiner* — Richard O Toohey
(74) *Attorney, Agent, or Firm* — ALSTON & BIRD LLP

(57) ABSTRACT

The present disclosure is directed to a composite film, comprising one or more layers, each layer comprising: i. a porous membrane comprising interconnected channels; and ii. a radiation sensitive material comprising a plurality of crystals, wherein the plurality of crystals are embedded in interconnected channels of said porous membrane. In certain embodiments, the radiation sensitive material is perovskite. Methods for producing the composite films and integrating the films onto read out circuitry for digital X-ray imaging are additionally described.

17 Claims, 12 Drawing Sheets

(58) Field of Classification Search
CPC ......... B32B 23/08; B32B 23/20; B32B 27/08; B32B 27/32; H10K 39/36; H10K 85/50
See application file for complete search history.

(56) References Cited

U.S. PATENT DOCUMENTS

2015/0251116 A1* 9/2015 Baer ................. B29C 48/71
    264/171.23
2019/0257959 A1* 8/2019 Thirimanne ............ G01T 1/241

OTHER PUBLICATIONS

Tan et al., "Vacuum-filtration enabled large-area CsPbBr 3 films on porous substrates for flexible photodetectors," Journal of Materials Chemistry, 7(43):13402-13409, (Oct. 2019).
WIPO Application No. PCT/2020/056140, PCT International Preliminary Report on Patentability mailed Apr. 19, 2022.
WIPO Application No. PCT/US2020/056140, PCT International Search Report and Written Opinion of the International Searching Authority mailed Feb. 2, 2021.

* cited by examiner

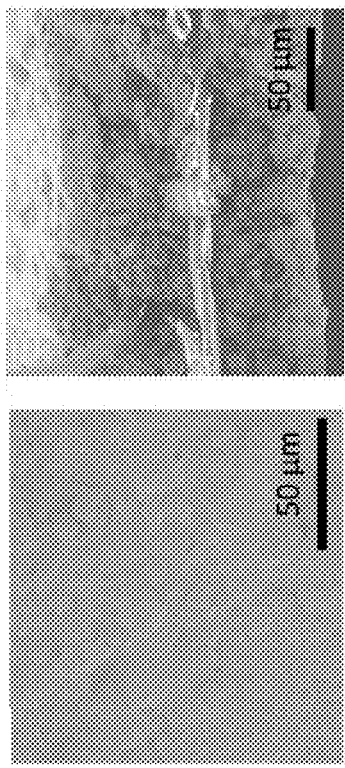
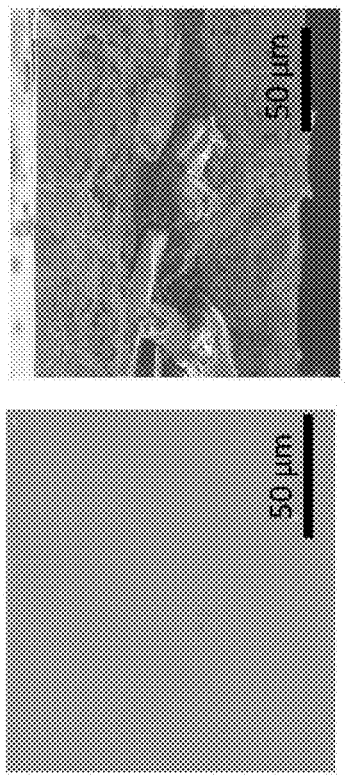

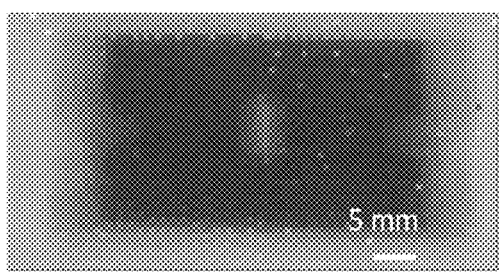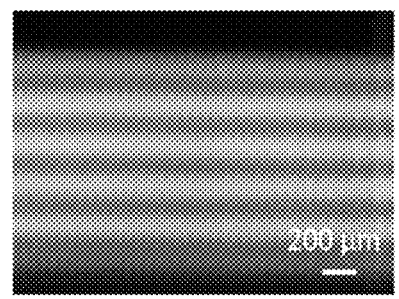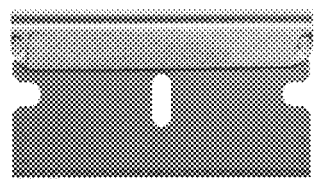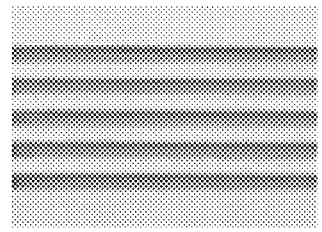
Fig. 7A
Fig. 7B

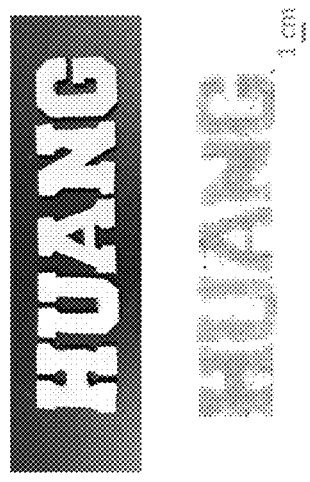
Fig. 8A
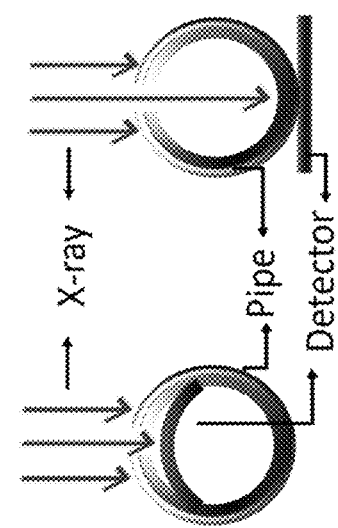
Fig. 8B
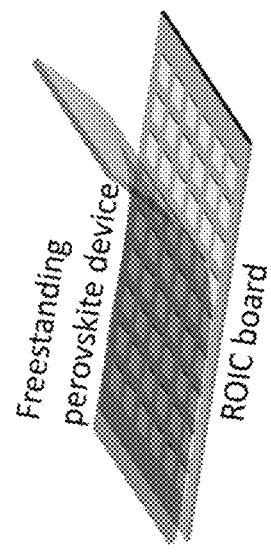
Fig. 8C
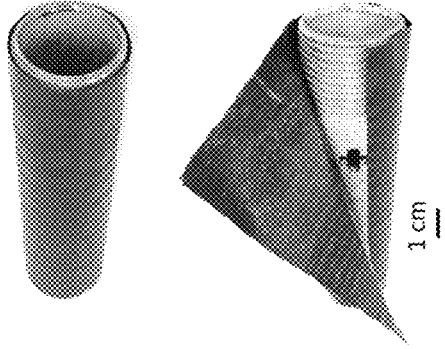

MEMBRANE-PEROVSKITE FILMS, DEVICES, AND METHODS OF PREPARATION

CROSS-REFERENCE TO RELATED APPLICATIONS

This application is a 35 U.S.C. § 371 national stage of International Application No. PCT/US2020/056140, filed Oct. 16, 2020, which claims the benefit of priority to U.S. Provisional Patent Application No. 62/923,037 filed on Oct. 18, 2019, the contents of which are incorporated by reference herein in their entirety for all purposes.

FIELD

The presently disclosed subject matter relates generally to composite films comprising a radiation sensitive material embedded in a porous membrane. In certain aspects, the radiation sensitive material is perovskite.

BACKGROUND

Radiation detectors play an important role in medical diagnostics, therapy, security screening, and scientific research. Perovskites are one avenue for emerging semiconductors for X-ray detection with high sensitivity and low cost. Perovskite single crystals are generally needed to achieve high sensitivity. However, it is difficult to synthesize single crystals directly on a read out circuit board with the minimum size needed for diagnostic medical imaging, such as computerized tomography. Mechanical flexibility is also desirable for X-ray detectors, especially for portable X-ray diagnostic tools. The majority of radiation detectors, however, are typically made of rigid inorganic materials. What is needed in the art is a flexible and robust conductive composite film for X-ray imaging. The methods described herein address this problem.

BRIEF SUMMARY

In one aspect, the subject matter described herein is directed to a multilayer composite film, comprising two or more layers, each layer comprising:
  i. a porous membrane comprising interconnected channels; and
  ii. a radiation sensitive material comprising a plurality of crystals, wherein the plurality of crystals are embedded in interconnected channels of said porous membrane;
  wherein said porous membrane and said radiation sensitive material in each adjacent layer are the same or different to those of any other layer; and said multilayer composite film is continuous.

In another aspect, the subject matter described herein is directed to a composite film, comprising one layer, said layer comprising:
  i. a porous membrane comprising interconnected channels; and
  ii. a radiation sensitive material comprising a plurality of crystals,
  wherein the plurality of crystals are embedded in interconnected channels of said porous membrane; and
  wherein said composite film is continuous.

In another aspect, the subject matter described herein is directed to an X-ray device comprising a continuous multilayer composite film or a continuous single layer composite film, and an electrode.

In another aspect, the subject matter described herein is directed to a method of preparing an integrated X-ray detector for use in digital x-ray imaging, said method comprising contacting an anisotropic conductive adhesive with a readout integrated circuit and contacting said anisotropic conductive adhesive with an X-ray detector.

In another aspect, the subject matter described herein is directed to an X-ray detector for use in digital x-ray imaging, wherein said X-ray detector further comprises an anisotropic conductive material and a readout integrated circuit, wherein said anisotropic conductive material is in fluid communication with said detector and said readout integrated circuit.

In another aspect, the subject matter described herein is directed to a method of preparing a multilayer composite film comprising two or more layers, said method comprising:
  a) passing a radiation sensitive material precursor solution through a porous membrane, wherein one or more crystals of the radiation sensitive material are retained in one or more pores of said porous membrane;
    wherein a) is carried out two or more times to prepare said two or more layers; wherein said radiation sensitive material precursor solution and said porous membrane in adjacent layers are the same or different; and
  b) compressing said two or more layers to prepare said continuous composite film.

In another aspect, the subject matter described herein is directed to a method of preparing a composite film comprising one layer, said method comprising:
  a) passing a radiation sensitive material precursor solution through a porous membrane, wherein one or more crystals of the radiation sensitive material are retained in one or more pores of said porous membrane; and
  b) compressing said layer to prepare said continuous composite film.

These and other aspects are described fully herein.

BRIEF DESCRIPTION OF THE DRAWINGS

FIG. 3A shows an in-plane SEM image of the perovskite-filled membrane before hot pressing.

FIG. 3B shows a cross section SEM image of the perovskite-filled membrane before hot pressing.

FIG. 3C shows an in-plane SEM image of the perovskite-filled membrane after hot pressing.

FIG. 3D shows a cross section SEM image of the perovskite-filled membrane after hot pressing.

FIG. 7A shows X-ray imaging of a razor blade.

FIG. 7B shows X-ray imaging of a Pb test phantom plate.

FIG. 8A shows a schematic diagram of the integration of a flexible free-standing x-ray detector to ROIC for digital imaging.

FIG. 8B shows a picture of the logo, "HUANG," and its digital imaging.

FIG. 8C shows a picture of a pipe with a cross hole and its x-ray imaging with configurations of the x-ray detector inside and outside of the pipe.

DETAILED DESCRIPTION

Figure 1A:
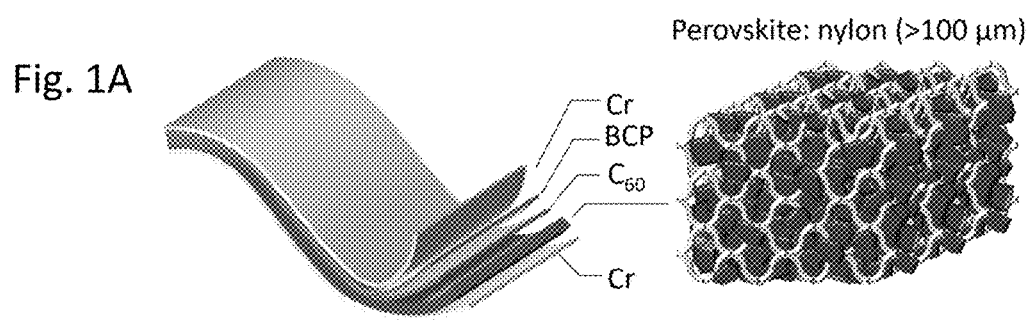
FIG. 1A shows a schematic diagram of a flexible perovskite x-ray detector.

The subject matter described herein relates to a single or multilayer composite film comprising a perovskite material embedded in a porous host membrane. The composite film can be rigid or flexible, depending on the host porous membrane and the desired application. Also presented are methods to prepare the composite films by passing a perovskite precursor solution through a porous membrane, followed by compressing with heat and pressure. These methods can generate dense, robust perovskite composite films with a mobility-lifetime product approaching that of single crystals. Methods of integrating the flexible perovskite composite films onto two dimensional read-out arrays is also presented using an anisotropic conductive adhesive, which allows for uni-direction electrical conduction. The X-ray images generated using the composite films exhibit a sensitivity comparable to those produced from single crystals.

Radiation detectors are commonly made of rigid inorganic materials such as amorphous selenium (α-Se),[1] thallium-doped cesium iodide (CsI:Tl),[2] Mercury iodide (HgI$_2$),[3] lead iodide (PbI$_2$),[4] terbium-doped gadoliniumoxysulfide (Gd2O2S:Tb)[5] and Cadmium (zinc) telluride (Cd(Zn)Te).[6] Among these materials, α-Se and CsI:Tl-based detectors dominate the market. α-Se X-ray detectors are commonly utilized in mammographs due to the material's low attenuation coefficient for hard X-rays. CsI:Tl detectors with a high stopping power are limited by potential light spreading in scintillators suffered by indirect X-ray detectors.[7] Organic-inorganic hybrid perovskites (OIHP) have shown potential as highly sensitive direct X-ray detectors due to their desired physical properties, including high atomic number (Pb, I), large carrier mobility, and high lifetime product (i). Solution processability and a compatible fabrication process using thin film transistors also provide perovskite radiation detectors with potential applications in large area flat panels. Furthermore, X-ray detectors based on perovskite single crystals have demonstrated over one thousand times higher sensitivity than commercial α-Se detectors.[8] Printable and sintered polycrystalline perovskite X-ray detectors have exhibited sensitivities in the range of 1000-11000 μC Gy$_{air}^{-1}$ cm$^{-2}$ and 2,527 μC Gy$_{air}^{-1}$ cm$^{-2}$ respectively.[9,10]

Flat panel radiation detection systems are typically cumbersome and fragile, which hinders their use in many applications—two examples being the oil and gas industry's difficult inspection of thick pipes and uncomfortable patient conditions in dental X-ray imaging. Flat radiation sensors also suffer from vignetting problems, which may result in misdiagnoses and errors in screening. As demonstrated herein, these vignetting problems can be eliminated by applying a curved detector without sacrificing any X-ray intensity. State-of-the art flexible X-ray detectors can be categorized into one of two classes: the first is based on solution-processed organic semiconductor materials fabricated on flexible substrates;[11,12] and the second is composed of rigid materials, which serve as pixels in the array amounted onto flexible substrates.[13,14] However, the former type of detectors, commonly consisting of low atomic number semiconductors, may exhibit low sensitivity.[11] The latter, conversely, may suffer from poor bendability and peeling following bending cycles, despite the complication in fabricating the arrays. In addition, the pixels may demonstrate non-uniform sensitivity and suffer from other performance parameter issues, such as high noise level, which requires additional pixel level imaging processing or hardware manipulation. To achieve adequate flexibility and avoid peeling problems, most flexible x-ray detectors have a thin film thickness that cannot effectively stop X-rays, resulting in much lower sensitivity of flexible X-ray detectors than that of their flat counterparts. For example, OIHP has been reported to be fabricated on flexible substrates wherein the active layer is only ~275 nm thick, which leads to very low sensitivity.[15]

Flexible organic inorganic hybrid composites with a thickness of around 20 μm have exhibited a volume sensitivity of 2.8*10$^5$ μC Gy$^{-1}$ cm$^{-3}$.[16] However, it is necessary to point out that the overall sensitivity of the X-ray detector is thickness dependent.[17,18] Conversely, organic crystal sensors cannot be thick due to the limited charge collection distance. Thus, the sensitivity of the best reported flexible detector is only around 560 μC Gy$_{air}^{-1}$ cm$^{-2}$, which is still much smaller than bulk single crystal perovskite detectors.

The subject matter described herein is directed to highly sensitive flexible solution-processed perovskite X-ray detectors. Being inserted into a mechanically strong membrane matrix, thick perovskite films can be fabricated to hundreds of micrometers thick, which can effectively stop X-rays, while also maintaining good flexibility. The sensitivity of the flexible X-ray detector approaches that of single crystalline perovskite X-ray detectors.

The presently disclosed subject matter will now be described more fully hereinafter. However, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims. In other words, the subject matter described herein covers all alternatives, modifications, and equivalents. Unless otherwise defined, all technical and scientific terms used herein have the same meaning as commonly understood by one of ordinary skill in this field. All publications, patent applications, patents, and other references mentioned herein are incorporated by reference in their entirety. In the event that one or more of the incorporated literature, patents, and similar materials differs from or contradicts this application, including but not limited to defined terms, term usage, described techniques, or the like, this application controls.

I. Definitions

As used herein, "and/or" refers to and encompasses any and all possible combinations of one or more of the associated listed items, as well as the lack of combinations when interpreted in the alternative ("or").

As used herein, the term "about," when referring to a measurable value such as an amount of a compound or agent of the current subject matter, dose, time, temperature, and the like, is meant to encompass variations of ±20%, ±10%, ±5%, ±1%, ±0.5%, or even ±0.1% of the specified amount.

The terms "approximately," "essentially," and "substantially" as used herein represent an amount close to the stated amount that still performs a desired function or achieves a desired result. For example, in some embodiments, as the context may dictate, the terms "approximately" and "substantially" may refer to an amount that is within less than or equal to 10% of the stated amount. The term "generally" as used herein represents a value, amount, or characteristic that predominantly includes or tends toward a particular value, amount, or characteristic.

As used herein, conditional language used herein, such as, among others, "can," "could," "might," "may," "e.g.," and the like, unless specifically stated otherwise or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

As used herein, "contacting" refers to physically contacting or connecting an anisotropic conductive film or an anisotropic conductive adhesive to a read out circuitry board or physically contacting or connecting an anisotropic conductive film or an anisotropic conductive adhesive to an X-ray detector. In certain other embodiments, "contacting" refers to allowing a radiation sensitive material to contact a porous membrane or allowing a melted material to contact pores of a membrane.

As used herein, "fluid communication" refers to the electrical contact between a read out circuitry board and an anisotropic conductive adhesive and between the anisotropic conductive adhesive and an X-ray detector.

As used herein, "porous" refers to a material that has pores, voids, or holes. The holes allow for the entry and flow of a liquid or gaseous material through the porous material. As used herein, a "porous membrane" refers to a membrane, matrix, scaffold, frame, or mold that comprises a porous surface with interconnected channels that pass throughout the core of the material.

As used herein, "interconnected" refers to a network comprising a series of connected channels. As used herein, the porous membranes comprise pores that are connected to one another by a series of channels that form an interconnected network. In certain embodiments, compressing the membranes by means of high pressures and temperatures are used to further integrate the interconnected channels by forcing the networks closer together.

As used herein, "plurality" refers to more than one and in certain embodiments, many. In certain embodiments, "plurality" is used to describe the relative quantity of crystals embedded in a porous membrane. In certain embodiments, the "plurality" of crystals is a number sufficient to cover the surface area inside the interconnected channels of the porous membrane.

As used herein, "crystal" refers to a crystalline solid material whose constituents (such as atoms, molecules, or ions) are arranged in a highly ordered microscopic structure, forming a crystal lattice that extends in all directions. Crystals can vary largely in size, depending on their growth conditions and their elemental components. As used herein, "microcrystal" refers to a crystal that is microscopic, having a size from about 50 nm to about 500 μm. In certain embodiments, the crystals are polyhedral.

As used herein, "embedded" or "reside" refers to being entrenched or deeply located within a void of a material. In certain embodiments, the void is an interconnected channel or a pore of a porous membrane.

As used herein, "flexible" refers to a composite film that can sustain its X-ray response while in a bending state. In certain embodiments, the flexible composite films as described herein can sustain their photocurrent when bent to a curvature with a radius of 2 mm.

As used herein, "smooth" refers to a composite film that has a uniform surface that is free of perceptible indentations or ridges.

As used herein, "compact" refers to a substantially void-free, densely-packed film.

As used herein, "continuous" refers to a composite film that exhibits a single-phase morphology.

As used herein, radiation sensitive materials are materials that are susceptible to undergoing a physical or chemical change when contacted with X-rays. In certain embodiments, the radiation sensitive materials described herein have a stopping power to X-rays of at least 20 KeV and exhibit good transport properties with carrier motilities of at least $10^5$ cm$^2$/V·s.

As used herein, "2ME" refers to 2-methoxyethanol.

II. Principles of Material Design

In one aspect, the presently described subject matter is directed to X-ray detectors comprising a flexible multilayer or single layer composite film. However, the materials can also be used for rigid, curved, and flat panel X-ray detectors. As described herein, porous, mechanically strong, but flexible membranes are used to host perovskite microcrystals for the fabrication of flexible perovskite composite X-ray detector films. By using a porous membrane matrix, perovskite films can be made to hundreds of micrometers thick, ensuring effective absorption of X-rays while also maintaining good flexibility. Perovskite microcrystals crystalize in the interconnected micro-channels of the membrane, forming a percolation path that ensures effective carrier transport and charge collection. Dense and fully filled perovskite membranes are desired. An elevated temperature and pressure can be applied to one or multiple films to fabricate dense, compact, robust, and large grain perovskite films. Perovskite microcrystals in the porous membranes are pressed to be close to each other. Meanwhile, the elevated temperatures help facilitate the grain growth of the perovskite microcrystals. The perovskite material can be filled into multiple membranes together or separately. Thus, it is possible to engineer the composition heterogeneity for a variety of purposes by modifying the perovskite composition in each layer. As further disclosed herein, several methods are demonstrated for integrating these flexible perovskite films onto read-out circuitry or on a back board using conductive adhesives.

III. Membranes

As described herein, the membrane is a solid, porous material. The pores of the membrane are filled with a radiation sensitive material, such as a perovskite material (FIG. 1A). The porous membrane structure is the backbone of the composite material, which provides mechanical support for the radiation sensitive material fillers. The porous membrane can therefore be flexible to allow for a flexible radiation detector, but can also be rigid, depending on the desired application.

In certain embodiments, the membrane has a pore size of about 10 nm to about 1 mm. In certain embodiments, the membrane has a pore size of about 10 nm to about 10 µm, about 1 µm to about 50 µm, about 1 nm to about 50 nm, about 5 µm to about 1 mm, or from about 25 µm to about 75 µm. In certain embodiments, the membrane has a pore size of about 3 µm, about 4 µm, about 5 µm, about 6 µm, about 7 µm, or about 8 µm.

In certain embodiments, the porous membrane has a thickness of about 10 µm to about 10 cm. In certain embodiments, the porous membrane has a thickness of about 10 µm to about 1 µm, about 10 µm to about 1 mm, about 1 µm to about 500 µm, or about 1 mm to about 10 mm. In certain embodiments, the membrane has a thickness of about 25 µm, about 50 µm, about 75 µm, about 100 µm, about 150 µm, about 200 µm, or about 250 µm.

In certain embodiments, the porous membrane comprises a material selected from the group consisting of metal, ceramic, polymer, carbon, protein, and a combination thereof.

In certain embodiments of a membrane comprising a polymer material, the material is selected from the group consisting nylon, low-density polyethylene (LDPE), high-density polyethylene (HDPE), polypropylene (PP), polyvinyl chloride (PVC), polyvinylidene fluoride (PVDF), polystyrene (PS), nylon, polytetrafluoroethylene (PTFE), polyimide, polyamide, polyacrilonitrile (PAN), polysulfone (PS), polyether sulfone (PES), cellulose, cellulose acetate, methyl cellulose, ethyl cellulose, nitrocellulose, hydroxylpropylcellulose (HPC), hydroxyethylcellulose (HEC), carboxymethylcellulose (CMC), polycarbonate (PCTE), polyether ether ketone (PEEK), and polydimethylsiloxane (PDMS).

In certain embodiments, the membrane comprises a combination of the above polymer materials. In certain embodiments, the polymer membrane is nylon. In certain embodiments, porous membranes comprising a polymer material are flexible.

In certain embodiments of a membrane comprising a ceramic material, the material is selected from the group consisting of alumina ($Al_2O_3$), titania ($TiO_2$), zirconium oxide ($ZrO_2$), silicon carbide (SiC), silicon dioxide ($SiO_2$), spinel ($MgAl_2O_4$), mullite selected from $3Al_2O_3$-$2SiO_2$ or $2Al_2O_3$-$SiO_2$, aluminum nitride (AlN), aluminum carbide ($Al_4C_3$), silicon nitride ($Si_3N_4$), silicon carbon nitride (SiCN), silicon aluminum carbon nitride (SiAlCN), zinc oxide (ZnO), Barium titanate ($BaTiO_3$), boron oxide, boron nitride, zirconium nitride (ZrN), titanium carbide (TiC), and titanium nitride (TiN). In certain embodiments, the membrane comprises a combination of the above ceramic materials.

In certain embodiments of a membrane comprising a metal material, the material is selected from the group consisting of Pd, Ag, Cu, Fe, Ni, W, Ti, Mo, Zn, Pt, Sn, Pb, Ga, Mg, Bi, Al, and stainless steel. Stainless steel refers to a steel alloy with a minimum of 11% chromium content by mass and a maximum of 1.2% carbon by mass. In certain embodiments, the stainless steel is selected from the group consisting of Type 304, Type 304L, Type 316, Type 316L, Type 201, Type 301, Type 305, Type 321, Type 347, Type 309S, Type 310S, Type 317L, Type 317LMN, Type 904L, Type 409, Type 405, Type 430, Type 434, Type 436, Type 439, Type 444, Type 26-3-3, Type 410, Type 420, Type 440A, Type 440C, Type 2304, Type 2205, Type 255, and Type 2507. In certain embodiments, the membrane comprises a combination of the above metal materials.

In certain embodiments of a membrane comprising a carbon material, the material is selected from the group consisting of carbon nanotubes (CNTs), carbon nanofibers (CNFs), graphene, carbon nanohorns (CNHs), carbon fiber, and carbon nanoparticles (CNPs). In certain embodiments, the membrane comprises a combination of the above carbon materials. In certain embodiments, porous membrane comprising a carbon material are flexible.

IV. Filler Materials

The active materials filling the membrane are radiation sensitive materials. In certain embodiments, the radiation sensitive material comprises a plurality of crystals. In certain embodiments, the radiation sensitive material is a perovskite compound having a formula of $ABX_3$.

In the perovskite formula of $ABX_3$, A is at least one cation selected from the group consisting of methylammonium, tetramethylammonium, formamidinium, cesium, rubidium, potassium, sodium, butylammonium, phenethylammonium, phenylammonium, and guanidinium.

In certain embodiments, A in $ABX_3$ is an ammonium, an organic cation of the general formula $[NR_4]^+$ where the R groups can be the same or different groups. Suitable R groups include, but are not limited to: methyl, ethyl, propyl, butyl, pentyl group or isomer thereof, any alkane, alkene, or alkyne $C_xH_y$, where x=1-20, y=1-42, cyclic, branched or straight-chain; alkyl halides, $C_xH_yX_z$, x=1-20, y=0-42, z=1-42, X=F, Cl, Br, or I; any aromatic group (e.g., phenyl, alkylphenyl, alkoxyphenyl, pyridine, naphthalene); cyclic complexes where at least one nitrogen is contained within the ring (e.g., pyridine, pyrrole, pyrrolidine, piperidine, tetrahydroquinoline); any sulfur-containing group (e.g., sulfoxide, thiol, alkyl sulfide); any nitrogen-containing group (nitroxide, amine); any phosphorous containing group (phosphate); any boron-containing group (e.g., boronic acid); any organic acid (e.g., acetic acid, propanoic acid); and ester or amide derivatives thereof, any amino acid (e.g., glycine, cysteine, proline, glutamic acid, arginine, serine, histindine, 5-ammoniumvaleric acid) including alpha, beta, gamma, and greater derivatives; any silicon containing group (e.g., siloxane); and any alkoxy or group, —OC$_x$H$_y$, where x=0-20, y=1-42. In certain embodiments, A is methylammonium, (CH$_3$NH$_3$$^+$).

In certain embodiments, A in ABX$_3$ is a formamidinium, an organic cation of the general formula [R$_2$NCHNR$_2$]$^+$ where the R groups can be the same or different groups. Suitable R groups include, but are not limited to: hydrogen, methyl, ethyl, propyl, butyl, pentyl or an isomer thereof, any alkane, alkene, or alkyne C$_x$H$_y$, where x=1-20, y=1-42, cyclic, branched or straight-chain; alkyl halides, C$_x$H$_y$X$_z$, x=1-20, y=0-42, z=1-42, X=F, Cl, Br, or I; any aromatic group (e.g., phenyl, alkylphenyl, alkoxyphenyl, pyridine, naphthalene); cyclic complexes where at least one nitrogen is contained within the ring (e.g., imidazole, benzimidazole, dihydropyrimidine, (azolidinylidenemethyl)pyrrolidine, triazole); any sulfur-containing group (e.g., sulfoxide, thiol, alkyl sulfide); any nitrogen-containing group (nitroxide, amine); any phosphorous containing group (phosphate); any boron-containing group (e.g., boronic acid); any organic acid (acetic acid, propanoic acid) and ester or amide derivatives thereof; any amino acid (e.g., glycine, cysteine, proline, glutamic acid, arginine, serine, histindine, 5-ammoniumvaleric acid) including alpha, beta, gamma, and greater derivatives; any silicon containing group (e.g., siloxane); and any alkoxy or group, OC$_x$H$_y$, where x=0-20, y=1-42.

In certain embodiments, A in ABX$_3$ is a guanidinium, an organic cation of the general formula [(R$_2$N)$_2$C=NR$_2$]$^+$ where the R groups can be the same or different groups. Suitable R groups include, but are not limited to: hydrogen, methyl, ethyl, propyl, butyl, pentyl group or isomer thereof, any alkane, alkene, or alkyne C$_x$H$_y$, where x=1-20, y=1-42, cyclic, branched or straight-chain; alkyl halides, C$_x$H$_y$X$_z$, x=1-20, y=0-42, z=1-42, X=F, Cl, Br, or I; any aromatic group (e.g., phenyl, alkylphenyl, alkoxyphenyl, pyridine, naphthalene); cyclic complexes where at least one nitrogen is contained within the ring (e.g., octahydropyrimido[1,2-a]pyrimidine, pyrimido[1,2-a]pyrimidine, hexahydroimidazo[1,2-a]imidazole, hexahydropyrimidin-2-imine); any sulfur-containing group (e.g., sulfoxide, thiol, alkyl sulfide); any nitrogen-containing group (nitroxide, amine); any phosphorous containing group (phosphate); any boron-containing group (e.g., boronic acid); any organic acid (acetic acid, propanoic acid) and ester or amide derivatives thereof, any amino acid (e.g., glycine, cysteine, proline, glutamic acid, arginine, serine, histindine, 5-ammoniumvaleric acid) including alpha, beta, gamma, and greater derivatives; any silicon containing group (e.g., siloxane); and any alkoxy or group, —OC$_x$H$_y$, where x=0-20, y=1-42.

In certain embodiments, A in ABX$_3$ is an alkali metal cation, such as Li$^+$, Na$^+$, K$^+$, Rb$^+$, or Cs$^+$.

In certain embodiments, the ABX$_3$ perovskite crystal structure composition may be doped (e.g., by partial substitution of the cation A and/or the metal B) with a doping element, which may be, for example, an alkali metal (e.g., Li$^+$, Na$^+$, K$^+$, Rb$^+$, or Cs$^+$), an alkaline earth metal (e.g., Mg$^{+2}$, Ca$^{+2}$, Sr$^{+2}$, Ba$^{+2}$) or other divalent metal, such as provided below for B, but different from B (e.g., Sn$^{+2}$, Pb$^{2+}$, Zn$^{+2}$, Cd$^{+2}$, Ge$^{+2}$, Ni$^{+2}$, Pt$^{+2}$, Pd$^{+2}$, Hg$^{+2}$, Si$^{+2}$, Ti$^{+2}$), or a Group 15 element, such as Sb, Bi, As, or P, or other metals, such as silver, copper, gallium, indium, thallium, molybdenum, or gold, typically in an amount of up to or less than about 1, 5, 10, 20, 25, 30, 35, 40, 45, 50, 55, 60, 65, 70, 75, 80, 85, 90, 95, 99, or 100 mol % of A or B. A may comprise a mixture of cations. B may comprise a mixture of cations.

The variable B in ABX$_3$ comprises at least one metal cation. In certain embodiments, B is a divalent metal atom. B can be, for example, one or more divalent elements from Group 14 of the Periodic Table (e.g., divalent lead, tin, or germanium), one or more transition metal elements from Groups 3-12 of the Periodic Table (e.g., divalent titanium, vanadium, chromium, manganese, iron, cobalt, nickel, copper, zinc, palladium, platinum, and cadmium), and/or one or more alkaline earth elements (e.g., divalent magnesium, calcium, strontium, and barium).

The variable X in ABX$_3$ is independently selected from one or a combination of halide atoms, wherein the halide atom (X) may be, for example, fluoride (F$^-$), chloride (Cl$^-$), bromide (Br$^-$), and/or iodide (I$^-$).

In certain embodiments, the radiation sensitive material is a perovskite material of ABX$_3$ selected from the group consisting of MAPbBr$_3$, MAPbI$_3$, and MAPb(I$_{0.9}$Cl$_{0.1}$)$_3$.

In certain embodiments, the radiation sensitive material is a perovskite compound having a formula of ABO$_3$, where A is a cation selected from the group consisting of Ba, Mg, Ca, Sr, La, Nd, Pr, Ce, Sm, Eu, Gd, Tb, Dy, Ho, Er, Yb, Lu, and a combination thereof, B is a metal cation selected from the group consisting of Si, Ti, Fe, Mn, Co, Ni, Al; and O is oxygen.

In certain embodiments, the radiation sensitive material is a perovskite compound having a formula of A$_2$B'B"X$_6$ where A is a cation selected from the group consisting of methylammonium (MA), tetramethylammonium, formamidinium (FA), cesium, rubidium, potassium, sodium, butylammonium, phenethylammonium, phenylammonium, guanidinium, ammonium, and a combination thereof, B' and B" are each independently a metal cation selected from the group consisting of lead, tin, cadmium, germanium, zinc, nickel, platinum, palladium, mercury, titanium, silicon, silver, copper, gold, calcium, bismuth, gallium, indium, antimony, and a combination thereof; and X is a halide selected from the group consisting of Cl, Br, F, I, and a combination thereof.

In certain embodiments, the radiation sensitive material is a compound selected from the group consisting of α-Se, CsI:Tl, HgI$_2$, PbI$_2$, Gd$_2$O$_2$S:Tb, (NH$_4$)3Bi2I9, and Cd(Zn)Te.

The crystals that fill the pores of the membrane are microcrystals. In certain embodiments, the microcrystals are crystals having a size of about 50 nm to about 500 micrometers. In certain embodiments, the crystals have a size of about 1 to 25 nm, about 5 to 100 micrometers, about 50 nm to about 10 micrometers, about 5 nm to about 250 micrometers, about 1 nm to about 100 micrometers, or about 10 micrometers to about 400 micrometers.

V. Stacking Composite Layers

Figure 1B:
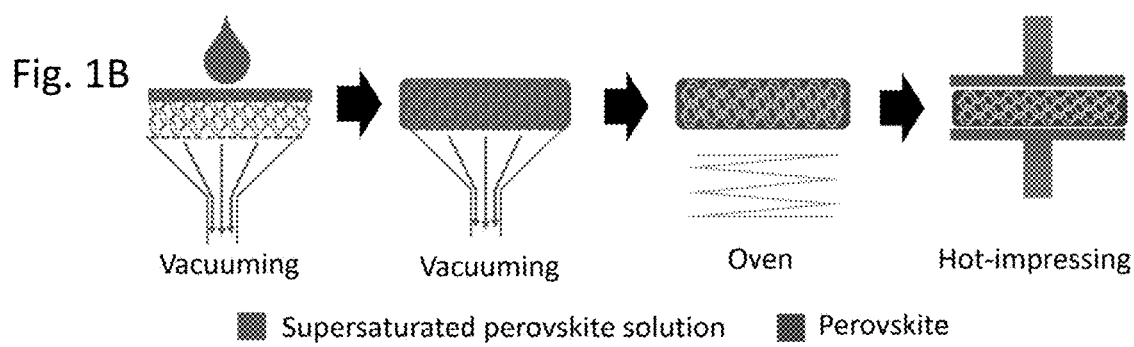
FIG. 1B shows the process of a perovskite-filled membrane.

In certain embodiments, a layer comprising a membrane further comprising a plurality of radiation sensitive material crystals embedded in the interconnected channels of the membrane can be stacked together with additional layers to form a multilayer composite film. As shown in FIG. 1B, layer n can be any integer from 1 to 10,000, from 1 to 5,000, from 1 to 500, from 1 to 250, from 1 to 100, from 1 to 50, from 1 to 15, from 1 to 10, from 1 to 7, from 1 to 5, or from 1 to 3. In certain embodiments, n is 1, 2, 3, 4, or 5.

The thickness of each of the layers is controllable and the compositions of the layers are adjustable. The composition of the membrane and the radiation sensitive material can be the same or different in adjacent layers. In certain embodiments, the thickness of each layer is from about 10 μm to about 10 cm, about 10 μm to about 1 μm, from about 1 μm to about 1 cm, from about 100 μm to about 400 μm, from about 150 μm to about 300 μm, from about 175 μm to about 275 µm, or from about 200 µm to about 250 µm. In certain embodiments, the thickness of the membrane layer is about 220 µm, about 130 µm, about 260 µm, or about 380 µm.

The crystalline composite films described herein have an average grain size of about 10 nm to about 1 mm. In certain embodiments, the crystalline films have an average grain size of about, at least, or above 0.01 m, 10 m, 20 m, 30 m, 40 m, 50 m, 60 m, 70 m, 80 am, 90 am, 100 am, 120 jm, 150 am, 180 am, 200 am, 220 am, 250 am, 280 am, 300 am, 350 am, 400 am, 450 am, 500 am, 550 am, 600 am, 650 am, 700 am, 800 am, 850 am, 900 am, 1000 am, or an average grain size within a range bounded by any two of the foregoing exemplary values.

In certain embodiments, the crystalline composite films described herein have a density from about 1 g/cm$^3$ to about 7 g/cm$^3$. In certain embodiments, the crystalline composite films described herein have a density from about 0.5 g/cm$^3$ to about 15 g/cm$^3$, about 1 g/cm$^3$ to about 5 g/cm$^3$, from about 0.75 g/cm$^3$ to about 8 g/cm$^3$, from about 2 g/cm$^3$ to about 6 g/cm$^3$, about 3 g/cm$^3$ to about 10 g/cm$^3$, about 5 g/cm$^3$ to about 10 g/cm$^3$, about 6 g/cm$^3$ to about 8 g/cm$^3$, or about 0.1 g/cm$^3$ to about 20 g/cm$^3$.

In certain embodiments, the crystalline composite films described herein have a density of about 1 g/cm$^3$, 2 g/cm$^3$, 3 g/cm$^3$, 4 g/cm$^3$, 5 g/cm$^3$, 6 g/cm$^3$, 7 g/cm$^3$, 8 g/cm$^3$, 9 g/cm$^3$, 10 g/cm$^3$, 11 g/cm$^3$, 12 g/cm$^3$, 13 g/cm$^3$, 14 g/cm$^3$, 15 g/cm$^3$, 16 g/cm$^3$, 17 g/cm$^3$, 18 g/cm$^3$, 19 g/cm$^3$, or 20 g/cm$^3$.

The density of the crystalline composite film refers to the density of the film after compressing. The density is a combination of the membrane and radiation sensitive filler material after compressing. In certain embodiments, the density of the film is determined by the density of a nylon membrane (1.15 g/cm$^3$) filled with a mixture of $ABX_3$ and $BX_2$ after compressing. In certain embodiments, the density of the film is determined by calculating the density of a nylon membrane (about 1.15 g/cm$^3$) filled with $PbI_2$ (about 6.16 g/cm$^3$) or $PbBr_2$ (about 6.66 g/cm$^3$), and/or $MAPbI_3$ (4.16 g/cm$^3$) after compressing. As described further herein, the composite films become smooth, dense, compact, and continuous after compressing. In certain embodiments, compressing can increase the density of the film from about 5-10%, 3-7%, 5-15%, 2-20%, 7-15%, 10-40%, 12-35%, 8-30%, 25-40%, or 15-50%. In certain embodiments, compressing can increase the density of the film by about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50%.

One method to achieve a high signal but with a suppressed dark current (or noise) involves placing highly X-ray sensitive materials (with high dark current) between two layers of less sensitive materials that have a lower dark current. For example, $MAPbBr_3$ has a lower dark current and exhibits less ion migration than that of $MAPbI_3$ due to its larger bandgap and its stronger bond energy of bromide with lead atoms. With a lower bandgap, the X-ray excited carriers of $MAPbI_3$ are more sensitive. Therefore, to generate a detector with a large signal to noise ratio, $MAPbI_3$ filled membranes can be positioned between two layers of $MAPbBr_3$. This is demonstrated in FIG. 2C, where a device with the mixed multilayer perovskite membrane structure of $MAPbBr_3$/$MAPb(I_{0.9}Cl_{0.1})_3$/$MAPb(I_{0.9}Cl_{0.1})_3$/$MAPbBr_3$ was fabricated.

VI. Composite Films

In certain embodiments, the composite film comprises four layers, wherein Layer 1 is adjacent to Layer 2; Layer 2 is adjacent to Layer 3; and Layer 3 is adjacent to Layer 4, wherein the porous membrane in each of the four layers is nylon, and each layer comprises a radiation sensitive material comprising a perovskite composition having the formula of $AB_X3$, wherein the perovskite composition in each layer is:

Layer 1: MAPbBr3
Layer 2: MAPb(I0.9Cl0.1)3
Layer 3: MAPb(I0.9Cl0.1)3
Layer 4: MAPbBr3.

In certain embodiments, the composite film comprises a single layer, wherein the porous membrane in the single layer film is nylon and the radiation sensitive material is a perovskite composition having a formula of $MAPb(I_{0.9}Cl_{0.1})_3$.

In certain embodiments, the composite film comprises a single layer, wherein the porous membrane in the single layer film is nylon and the radiation sensitive material is a perovskite composition having a formula of MAPbBr3.

VII. Fabrication Process

Process for Filling Membranes
Method 1

In certain embodiments, under an applied pressure, the radiation sensitive material can melt and effectively fill the pores of the porous membrane. In certain embodiments, a high temperature may be used in conjunction with the applied pressure to facilitate the melting process. After melting, the materials solidify in the membrane following a period of cooling. This method is especially effective for materials that cannot easily dissolve in solvent.

Method 2

In certain embodiments, the radiation sensitive materials are dissolved in one or more solvents to prepare a precursor solution. In certain embodiments, the precursor solution is passed through the membrane, as shown in FIG. 1B. In certain embodiments, the precursor solution is immersed in the membrane. In certain embodiments, the membrane is first immersed in the radiation sensitive precursor solution and then the radiation sensitive precursor solution is passed through the porous membrane.

In certain embodiments, the radiation sensitive material precursor solution is a perovskite precursor solution. For perovskite composite films, a high filling ratio of perovskite crystals residing in the membrane is desired to effectively stop X-rays. In certain embodiments, a saturated or near-saturated perovskite precursor solution is used to enhance the filling ratio of the material in the membrane. In certain embodiments, passing the precursor solution several times through the membrane is carried out to facilitate the filling ratio of the radiation sensitive material in the membrane. In certain embodiments, high concentrations of the precursor solution facilitate a greater amount of perovskite material to be deposited into the membrane. It was discovered that the perovskite precursor saturated solution can be prepared up to 3 M by mixing in a 10% molar ratio of MACl (MA=methylammonium), as described in Example 1.

In certain embodiments, passing the precursor solution through the membrane is accompanied by a pressure difference between two sides of the membrane. In certain embodiments, the pressure difference is achieved by using a mechanical pump, syringe, or other suitable apparatus. In certain embodiments, the pressure difference is between 2 psi and 20 psi, 4 psi to 10 psi, 3 psi to 50 psi, or 15 psi to 25 psi.

Crystals from the radiation sensitive material precursor solution reside in the membrane once the solution is passed through the membrane. In certain embodiments, thermal annealing, vacuuming, gas blowing, or anti-solvent immersing/filtering facilitate crystal formation.[19] In certain embodiments annealing is carried out to facilitate crystal formation.

In certain embodiments, annealing is at a temperature of at least or above 30° C. In certain embodiments, annealing is at least, above, up to, or less than 40° C., 50° C., 60° C., 70° C., 80° C., 90° C., 100° C., 110° C., 120° C., 130° C., 140° C., 150° C., 160° C., 170° C., 180° C., 190° C., 200° C., 210° C., 220° C., 230° C., 240° C., 200° C. or a temperature within a range bounded by any two of the foregoing values. In various embodiments, annealing is in a range of 10-300° C., 30-200° C., 50-150° C., 30-180° C., 30-150° C., 30-140° C., 30-130° C., 30-120° C., 30-110° C., or 30-100° C.

In certain embodiments, annealing is carried out for about 0 seconds to 400 minutes, about 5 seconds to 30 seconds, about 5 minutes to about 10 minutes, about 10 minutes to 20 minutes, or about 20 minutes to 30 minutes. In certain embodiments, annealing is carried out for at least 5 seconds, 10 seconds, 20 seconds, 30 seconds, 1 minute, 5 minutes, 10 minutes, 20 minutes, 30 minutes, 60 minutes, 90 minutes, 120 minutes, 180 minutes, 240 minutes, or 360 minutes.

In certain embodiments, where the radiation sensitive material precursor solution is a perovskite precursor solution, the perovskite precursor solution is prepared by dissolving a perovskite compound of formula $ABX_3$ in one or more solvents selected from the group consisting of dimethyl sulfoxide, dimethylformamide, γ-butyrolactone, 2-methoxyethanol, and acetonitrile. In certain embodiments, the solvent is 2-methoxyethanol. In certain embodiments, the perovskite precursor solution comprises a compound of formula $ABX_3$ and a compound of formula AX, wherein A is at least one monovalent cation selected from the group consisting of methylammonium, tetramethylammonium, formamidinium, guanidinium, cesium, rubidium, potassium, sodium, butylammonium, phenethylammonium, and phenylammonium; X is selected from the group consisting of halide, acetate ($CH_3CO_2^-$), and thiocyanate ($SCN^-$). In certain embodiments, the compound of formula AX is MACl and the compound of formula $ABX_3$ is $MAPbBr_3$. In certain embodiments, the compound of formula AX is MACl and the compound of formula $ABX_3$ is $MAPb(I_{0.9}Cl_{0.1})_3$. In certain embodiments, the compound of formula AX is added the perovskite precursor solution in molar ratio of about 5% to about 15%. In certain embodiments, the compound of formula AX is added the perovskite precursor solution in molar ratio of about 7%, about 8%, about 9%, about 10%, about 11%, or about 12%.

In certain embodiments, the perovskite precursor solution comprises a compound of formula $BX'_2$, wherein B is a least one divalent metal and X' is a monovalent anion; a compound of formula AX, wherein A is at least one monovalent cation selected from the group consisting of methylammonium, tetramethylammonium, formamidinium, guanidinium, cesium, rubidium, potassium, sodium, butylammonium, phenethylammonium, and phenylammonium; X is selected from the group consisting of halide, acetate ($CH_3CO_2^-$), and thiocyanate ($SCN^-$); and one or more solvents selected from the group consisting of dimethyl sulfoxide, dimethylformamide, γ-butyrolactone, 2-methoxyethanol, and acetonitrile. In certain embodiments, the solvent is 2-methoxyethanol.

In certain embodiments, the perovskite precursor solution comprises a compound of formula $BX'_2$, wherein B is selected from the group consisting of lead, tin, cadmium, germanium, zinc, nickel, platinum, palladium, mercury, titanium, and silicon. In certain embodiments, the perovskite precursor solution comprises a compound of formula $BX'_2$, wherein B is lead or tin. In certain embodiments, the perovskite precursor solution comprises a compound of formula $BX'_2$, wherein the divalent metal B comprises lead. In certain embodiments, the perovskite precursor solution comprises a compound of formula $BX'_2$, wherein the divalent metal B is lead.

In the compound of formula $BX'_2$, the monovalent anion X' can be any anionic species. In certain embodiments, the monovalent anion X' is a halide. Some examples of anionic species X', other than halide species, include formate, acetate, propionate, carbonate, nitrate, sulfate, thiosulfate, oxalate, triflate, cyanate, thiocyanate, acetylacetonate, and 2-ethylhexanoate. Some examples of compounds of formula $BX'_2$ include the following: lead(II) fluoride, ($PbF_2$); lead(II) chloride, ($PbCl_2$); lead(II) bromide, ($PbBr_2$); lead(II) iodide, ($PbI_2$); lead(II) acetate, ($Pb(CH_3CO_2)_2$) or ($PbAc_2$); lead(II) carbonate, ($PbCO_3$); lead(II) nitrate, ($Pb(NO_3)_2$); lead(II) sulfate, ($PbSO_4$); lead(II) oxalate, ($PbC_2O_4$); lead(II) triflate, ($C_2F_6O_6PbS_2$); lead(II) thiocyanate, ($Pb(SCN)_2$), lead(II) acetylacetonate, ($Pb(C_5H_7O_2)_2$); lead(II) 2-ethylhexanoate, ($C_{16}H_{30}O_4Pb$); tin(II) fluoride, ($SnF_2$), tin(II) chloride, ($SnCl_2$); tin(II) bromide, ($SnBr_2$); tin(II) iodide, ($SnI_2$); tin(II) acetate, ($Sn(CH_3CO_2)_2$) or ($SnAc_2$); tin(II) carbonate, ($SnCO_3$); tin(II) nitrate, ($Sn(NO_3)_2$); tin(II) sulfate, ($SnSO_4$); tin(II) oxalate, ($SnC_2O_4$); tin(II) triflate, ($C_2F_6O_6SnS_2$); tin(II) thiocyanate, ($Sn(SCN)_2$); tin(II) acetylacetonate, ($Sn(C_5H_7O_2)_2$); tin(II) 2-ethylhexanoate, ($C_{16}H_{30}O_4Sn$); germanium(II) chloride, ($GeCl_2$); germanium(II) bromide, ($GeBr_2$); germanium (II) iodide, ($GeI_2$); titanium(II) chloride, ($TiCl_2$); titanium(II) bromide, ($TiBr_2$); titanium(II) iodide, ($TiI_2$); titanium(II) acetate, (Ti($CH_3CO_2)_2$); magnesium fluoride, ($MgF_2$); magnesium chloride, ($MgCl_2$); magnesium bromide, ($MgBr_2$); magnesium iodide, ($MgI_2$); magnesium acetate, ($Mg(CH_3CO_2)_2$); magnesium sulfate, ($MgSO_4$); calcium fluoride, ($CaF_2$); calcium chloride, ($CaCl_2$); calcium bromide, ($CaBr_2$); calcium iodide, ($CaI_2$); calcium acetate, ($Ca(CH_3CO_2)_2$); calcium sulfate (CaSO4), cadmium (II) chloride ($CdCl_2$); cadmium (II) bromide ($CdBr_2$); cadmium (II) iodide ($CdI_2$); zinc (II) chloride ($ZnCl_2$); zinc (II) bromide ($ZnBr_2$); zinc (II) iodide ($ZnI_2$); platinum (II) chloride ($PtCl_2$); platinum (II) bromide ($PtBr_2$); platinum (II) iodide ($PtI_2$); nickel (II) chloride ($NiCl_2$); Nickel (II) bromide ($NiBr_2$); nickel (II) iodide ($NiI_2$); palladium (II) chloride ($PdCl_2$); palladium (II) bromide ($PdBr_2$); palladium (II) iodide ($PdI_2$); mercury (II) chloride ($HgCl_2$); mercury (II) bromide ($HgBr_2$); and mercury (II) iodide ($HgI_2$).

In certain embodiments, the formula $BX'_2$ is selected from the group consisting of $PbI_2$, $PbBr_2$, $PbCl_2$, $SnJ_2$, $SnBr_2$, and $SnCl_2$.

In the formula AX, the cation species A is at least one monovalent cation selected from the group consisting of methylammonium, tetramethylammonium, formamidinium, guanidinium, cesium, rubidium, potassium, sodium, butylammonium, phenethylammonium, and phenylammonium; and X is selected from the group consisting of halide, acetate ($CH_3CO_2^-$), and thieocyanate ($SCN^-$). In certain embodiments, X is a halide. Several nonlimiting examples of compounds of Formula AX include methylammonium fluoride, methylammonium chloride, methylammonium bromide, methylammonium iodide, tetramethylammonium fluoride, tetramethylammonium chloride, tetramethylammonium bromide, tetramethylammonium iodide, formamidinium chloride, formamidinium bromide, formamidinium iodide, guanidinium fluoride, guanidinium chloride, guanidinium bromide, guanidinium iodide, cesium iodide, cesium bromide, cesium chloride, butylammonium iodide, butylammonium bromide, butylammonium chloride, phenethylammonium iodide, phenethylammonium bromide, phenethylammonium chloride, phenylammonium iodide, phenylammonium bromide, and phenylammonium chloride. In certain embodiments, the compound of formula AX is selected from the group consisting of methylammonium iodide, methylammonium bromide, methylammonium chloride, formamidinium iodide, formamidinium bromide, formamidinium chloride, cesium iodide, cesium bromide, cesium chloride, butylammonium iodide, butylammonium bromide, butylammonium chloride, phenethylammonium iodide, phenethylammonium bromide, phenethylammonium chloride, phenylammonium iodide, phenylammonium bromide, and phenylammonium chloride. In certain embodiments, the compound of formula AX is selected from the group consisting of methylammonium iodide, cesium iodide, formamidinium iodide, butylammonium iodide, phenethylammonium iodide, methylammonium bromide, cesium bromide, formamidinium bromide, butylammonium bromide, and phenethylammonium iodide. In certain embodiments, the compound of formula AX is methylammonium chloride.

In certain embodiments, $BX'_2$ is $PbCl_2$ and AX is methylammonium chloride. In certain embodiments, $BX'_2$ is $PbBr_2$ and AX is methylammonium bromide. In certain embodiments, $BX'_2$ is $PbI_2$ and AX is methylammonium iodide.

In certain embodiments, $BX'_2$ and AX in the precursor are generally present in a molar ratio of M:X of about 1:3. In certain embodiments, in the case where X' is a halide X, which corresponds with $BX'_2$ being $BX_2$, then a B:X molar ratio of about 1:3 can be provided by a 1:1 molar ratio of $BX_2$:AX. In certain embodiments, in the case where X' is non-halide (e.g., acetate), then a B:X molar ratio of about 1:3 can be provided by a 1:3 molar ratio of $BX'_2$:AX.

In certain embodiments, the perovskite precursor solution comprises a compound of formula AX, $BX'_2$, and the contact products thereof. As used herein, "contact products" refer to the compositions of matter that may result when AX and $BX'_2$ contact each other. In certain embodiments, a contact product is a perovskite compound of the formula $ABX_3$. In certain embodiments, the perovskite precursor solution comprises a compound of the formula $ABX_3$.

In certain embodiments, the relative amount of $ABX_3$ to $BX'_2$ and AX is about 99:1. In certain embodiments, the relative amount of $ABX_3$ to $BX'_2$ and AX is about 80:20, about 70:30, about 50:50, about 30:70, about 20:80, or about 1:99.

In certain embodiments, one or more additives are used in the precursor solution to increase the solubility of the perovskite. Non-limiting examples of additives are methylammonium ion ($MA^+$), n-butylammonium ion ($BA^+$), phenylethylammonium ion ($PEA^+$), formamidinium ($FA^+$), $Cs^+$, $Li^+$, $Na^+$, and anions including $I^-$, $Br^-$, $Cl^-$, thiocyanate ($SCN^-$), and acetate ($CH_3CO^-_2$). In certain embodiments, a combination of the above additives may be used in the precursor solution.

Compressing Process

In certain embodiments, after the radiation sensitive material precursor solution is passed through the membrane, wherein one or more crystals of the radiation sensitive material resides in one or more pores of the porous membrane, compressing is applied to enhance the density of the membrane. In certain embodiments, compressing comprises applying a pressure and a temperature to one of more membrane-filled layers. In certain embodiments, compressing is referred to as "hot pressing."

In certain embodiments, the compressing pressure is from about 0.1 MPa to about 10 GPa. In certain embodiments, the pressure is from about 1 Pa to about 1 KPa, from about 1 KPa to about 1 MPa, from about 0.25 MPa to about 10 MPa, from about 2 MPa to about 8 MPa, from about 10 Pa to about 10 GPa, or from about 1 MPa to about 5 MPa. In certain embodiments, the pressure is about 0.5 MPa or about 2 MPa.

In certain embodiments, the compressing temperature is from about from about 300 K to about 3000 K. In certain embodiments, the temperature is from about 280 K to about 350 K, from about 250 K to about 400K, from about 500 K to about 2000 K, from about 700 K to about 1000 K, or from about 600 K to about 1500 K. In certain embodiments, the temperature is about 35° C. (308.15 K) or about 200° C. (473.15 K).

Compressing can take place for about 0 seconds to 8000 minutes, about 5 seconds to about 30 seconds, about 5 minutes to about 10 minutes, about 10 minutes to about 20 minutes, or about 20 minutes to about 30 minutes. Compressing can take place for at least 5 seconds, 10 seconds, 20 seconds, 30 seconds, 1 minute, 5 minutes, 10 minutes, 20 minutes, 30 minutes, 60 minutes, 90 minutes, 120 minutes, 180 minutes, 240 minutes, 380 minutes, 450 minutes, 800 minutes, 1200 minutes, 2000 minutes, 2700 minutes, 3500 minutes, 4500 minutes, 6000 minutes, 7000 minutes, or 8000 minutes. In certain embodiments, compressing takes place for 90 seconds. In certain embodiments, compressing takes place for 120 seconds.

The compressing processing can be carried out in one step or multiple steps. The pressure, temperature and time parameters are not coupled and can be different in each step.

In certain embodiments, a template is used for hot pressing. The template can be any substrate with a smooth, flat surface. In certain embodiments, the template comprises two glass slides with flat smooth surfaces. In certain embodiments, the template comprises a material selected from the group consisting of glass slides, silicon wafers, and stainless steel plates.

In certain embodiments, the template is treated with plasma prior to hot pressing. In certain embodiments, the plasma is selected from the group consisting of ozone plasma, argon plasma, air plasma, and nitrogen plasma. In certain embodiments, the template is treated with ozone plasma. In certain embodiments, a hydrophobic material is deposited onto the template prior to annealing. In certain embodiments, the hydrophobic material is selected from the group consisting of heptadecafluoro-1,1,2-2-tetrahydrodecyl)triethoxysilane, (3,3,3-trifluoropropyl)trimethoxysilane, heptadecafluoro-1,1,2-2-tetrahydrodecyl)trimethoxysilane; heptadecafluoro-1,1,2-2-tetrahydrodecyl) trichlorosilane, (tridecafluoro-1,1,2,2-tetrahydrooctyl) triethoxysilane, (perfluoroalkyl)ethyltriethoxysilane, and trichloro(3 3 3-trifluoropropyl)silane. In certain embodiments, the hydrophobic material is trichloro(3 3 3-trifluoropropyl)silane. In certain embodiments, a methylammonium halide solvent solution is deposited on the template prior to hot pressing. In certain embodiments, the methylammonium halide solvent solution is methylammonium iodide in isopropanol. The hydrophobic material and the methylammonium halide solvent solution may be deposited on the template by a suitable means, including, but not limited to, doctor blading, slot die coating, shear coating, gravure coating, spin casting, brush coating, syringe coating, and screen printing.

In certain embodiments, the composite films produced have an area of at least 1 cm$^2$, 2 cm$^2$, 3 cm$^2$, 4 cm$^2$, 5 cm$^2$, 6 cm$^2$, 7 cm$^2$, 8 cm$^2$, 9 cm$^2$, 10 cm$^2$, 11 cm$^2$, 12 cm$^2$, 13 cm$^2$, 14 cm$^2$, 15 cm$^2$, 17 cm$^2$, 20 cm$^2$, 22 cm$^2$, 25 cm$^2$, 27 cm$^2$, 30 cm$^2$, 35 cm$^2$, 40 cm$^2$, 45 cm$^2$ 50 cm$^2$, 55 cm$^2$, 60 cm$^2$, 75 cm$^2$, 80 cm$^2$, 85 cm$^2$, 100 cm$^2$, 125 cm$^2$, 150 cm$^2$, 200 cm$^2$, 225 cm$^2$, 250 cm$^2$, 275 cm$^2$, 300 cm$^2$, 325 cm$^2$, or 350 cm$^2$.

Free-Standing Flexible X-Ray Detector

In certain embodiments, the subject matter described herein is directed to an X-ray device comprising a continuous multilayer composite film or a continuous single layer composite film, and an electrode. In other embodiments, the X-ray device comprises two electrodes. In certain embodiments, the electrodes are each Cr. In other embodiments, the electrode(s) is/are selected from lithium, sodium, potassium, rubidium, cesium, francium, beryllium, magnesium, calcium, strontium, barium, radium, boron, aluminum, gallium, indium, thallium, tin, lead, flerovium, bismuth, antimony, tellurium, polonium, scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, rutherfordium, dubnium, seaborgium, bohrium, hassium, copernicium, samarium, neodymium, ytterbium, an alkali metal fluoride, an alkaline-earth metal fluoride, an alkali metal chloride, an alkaline-earth metal chloride, an alkali metal oxide, an alkaline-earth metal oxide, a metal carbonate, a metal acetate, carbon nanowire, carbon nanosheet, carbon nanorod, carbon nanotube, graphite, indium tin oxide (ITO), fluorine-doped tin oxide (FTO), aluminum doped zinc oxide (AZO), antimony-tin mixed oxide (ATO), network of metal/alloy nanowire, or a combination of two or more of the above materials In certain embodiments, the subject matter described herein is directed to an X-ray device comprising a single or multilayer composite film having a density of about 1 g/cm$^3$ to about 7 g/cm$^3$, wherein the X-ray device further comprises a detector or a panel. In certain embodiments, the single or multilayer composite film is a photoactive layer in an X-ray detector. In certain embodiments, the X-ray detector comprising the single or multilayer composite film is a free-standing, flexible X-ray detector.

In certain embodiments, the X-ray detector comprises first and second electrodes (i.e. a cathode and an anode or vice versa), an active layer, and one or more charge transport layers.

In certain embodiments, the cathode and anode (each electrode) each comprise at least one of lithium, sodium, potassium, rubidium, cesium, francium, beryllium, magnesium, calcium, strontium, barium, radium, boron, aluminum, gallium, indium, thallium, tin, lead, flerovium, bismuth, antimony, tellurium, polonium, scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, rutherfordium, dubnium, seaborgium, bohrium, hassium, copernicium, samarium, neodymium, ytterbium, an alkali metal fluoride, an alkaline-earth metal fluoride, an alkali metal chloride, an alkaline-earth metal chloride, an alkali metal oxide, an alkaline-earth metal oxide, a metal carbonate, a metal acetate, carbon nanowire, carbon nanosheet, carbon nanorod, carbon nanotube, graphite, indium tin oxide (ITO), fluorine-doped tin oxide (FTO), aluminum doped zinc oxide (AZO), antimony-tin mixed oxide (ATO), network of metal/alloy nanowire, or a combination of two or more of the above materials. In certain embodiments, the anode is chromium. In certain embodiments, the cathode is chromium.

In certain embodiments, the charge transport layer between the active layer and the cathode comprises at least one of poly(3,4-ethylene dioxithiophene) (PEDOT) doped with poly(styrene sulfon icacid) (PSS), Spiro-OMeTAD, pm-spiro-OMeTAD, po-spiro-OMeTAD, dopants in spiro-OMeTAD, 4,4'-biskptrichlorosilylpropylphenyl)pheny laminoThiphenyl (TPD-Si2), poly(3-hexyl-2,5-thienylene vinylene) (P3HTV), C60, carbon, carbon nanotube, graphene quantum dot, graphene oxide, copper phthalocyanine (CuPc), Polythiophene, poly(3,4-(1hydroxymethyl)ethylenedioxythiophene) (PHMEDOT), n-dodecylbenzenesulfonic acid/hydrochloric acid doped poly(aniline) nanotubes (a-PANIN)s, poly(styrene sulfonic acid)-graft-poly(aniline) (PSSA-g-PANI), poly(9. 9-dioctylfluorene)-co-N-(4-(1-methylpropyl)phenyl) diphenylamine (PFT), 4,4'-bis(p-trichlorosilylpropylphenyl) phenylaminobiphenyl (TSPP), 5,5'-bis(p-trichlorosilylpropylphenyl) phenylamino-2,20 bithiophene (TSPT), N-propyltriethoxysilane, 3,3,3-trifluo ropropyltrichlorosilane or 3-aminopropyltriethoxysilane, Poly(bis(4-phenyl)(2,4,6-trimethylphenyl)amine) (PTAA), (Poly[[(2,4-dimethylphenyl)imino]-1,4-phenylene(9,9-di-octyl-9H-fluorene-2,7-diyl)-1,4phenylene], (PF8-TAA)), (Poly [[(2,4-dimethylphenyl)imino]-1,4-phenylene (6,12-dihydro-6,6,12,12tetraoctylindeno[1,2-b]fluorene-2,8-diyl)-1,4-phenylene]) (PIF8-TAA), poly[[4,8-bis[(2-ethylhexyl)oxy]benzo[1,2-b:4,5-b]dithiophene-2,6-diyl][3-fluoro-2-[(2-ethylhexyl)carbonyl]thieno[3,4-b]thiophenediyl]] (PTB7), poly[N-90-heptadecanyl-2,7-carbazole-alt-5,5-(40, 70-di-2-thienyl-20,10,30-benzothiadiazole)] (PCDTBT), Poly[2,5-bis(2-decyldodecyl)pyrrolo[3,4-c]pyrrole-1,4(2H, 5H)-dione-(E)-1,2-di(2,20-bithiophen-5-yl) ethene] (PDPPDBTE), 4,8-dithien-2-yl-benzo[1,2-d;4,5-d']bistriazole-alt-benzo[1,2-b:4,5b']dithiophenes (pBBTa-BDTs), pBBTa-BDT1, pBBTa-BDT2 polymers, poly(3-hexylthiophene) (P3HT), poly(4,4'-bis(N-carbazolyl)-1,1'-biphenyl) (PPN), triarylamine (TAA) and/or thiophene moieties, Paracyclophane, Triptycene, and Bimesitylene, Thiophene and Furan-based hole transport materials, Dendrimer-like and star-type hole transport materials, VO, VOX, MoC, WO, ReO, NiOx, AgOx, CuO, Cu2O, V2O5, CuI, CuS, CuInS2, colloidal quantum dots, lead sulphide (PbS), CuSCN, Cu2ZnSnS4, Au nanoparticles and their derivatives. Thiophene derivatives, Triptycene derivatives, Triazine derivatives, Porphyrin derivatives, Triphenylamine derivatives, Tetrathiafulvalene derivatives, Carbazole derivatives and Phthalocyanine derivatives. As used herein, when a material is referred to a "derivate" or as "derivatives," such as Triphenylamine derivatives, the material contains Triphenylamine in its backbone structure.

In certain embodiments, the charge transport layer between active layer and the anode comprises at least one of LiF, CsP, LiCoO, CsCO, TiOX, TiO, nanorods (NRs), ZnO, ZnO nanorods (NRs), ZnO nanoparticles (NPs), ZnO, Al—O, CaO, bathocuproine (BCP), copper phthalocyanine (CuPc), pentacene, pyronin B, pentadecafluorooctyl phenyl-C60-butyrate (F-PCBM), C60, C60/LiF, ZnO NRS/PCBM, ZnO/cross-linked fullerene derivative (C-PCBSD), single walled carbon nanotubes (SWCNT), poly(ethylene glycol) (PEG), poly(dimethylsi loxane-block-methyl methacrylate) (PDMS-b-PMMA), polar polyfluorene (PF-EP), polyfluorene bearing lateral amino groups (PFN), polyfluorene bearing quaternary ammonium groups in the side chains (WPF-oxy-F), polyfluo rene bearing quaternary ammonium groups in the side chains (WPF-6-oxy-F), fluorene alternating and random copolymer bearing cationic groups in the alkyl side chains (PFNBr DBT15), fluorene alternating and random copolymer bearing cationic groups in the alkyl side chains (PFPNBr), poly (ethylene oxide) (PEO), and fullerene derivatives.

In certain embodiments, the X-Ray detector has the structure, Cr/MAPb($I_{0.9}Cl_{0.1}$)$_3$/$C_{60}$/BCP/Cr.

In certain embodiment, the subject matter described herein is directed to an X-ray detector comprising a continuous multilayer composite film or a continuous single layer composite film, a transport layer, a first electrode, and a second electrode, wherein said composite film is disposed on said first electrode, said transport layer is disposed on said composite film, and said second electrode is disposed on said transport layer. In embodiments, said composite film is MAPb($I_{0.9}Cl_{0.1}$)$_3$, said first and second electrodes are Cr, and said transport layer comprises two layers comprising a $C_{60}$ layer and a BCP layer, wherein said $C_{60}$ layer is disposed on said composite film and said BCP layer is disposed on said $C_{60}$, wherein said second electrode is disposed on said BCP.

In certain embodiments, the thickness of the device is from about 1 µm to about 800 µm, from about 50 µm to about 600 µm, or from about 100 µm to about 400 µm. In certain embodiments, the device is about 100 µm to about 400 µm, from about 150 µm to about 300 µm, from about 175 µm to about 275 µm, or from about 200 µm to about 250 µm. In certain embodiments, the device thickness is about 220 µm, about 130 µm, about 260 µm, or about 380 µm.

In certain embodiments, the device exhibits a stable X-ray current when bent to a curvature of at least 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm.

Integration of Flexible X-ray Detector on Readout Integrated Circuit (ROIC)

The free-standing X-ray detector can be integrated on a readout system for digital X-ray imaging. Commercial ROICs can be purchased from, for example, Teledyne Scientific Company or Voxtel, Inc. In certain embodiments, the device is fabricated as a single pixel. In certain embodiments, the device is fabricated as linear pixels. In certain embodiments, the device is fabricated as matrix pixels.

Figure 4:
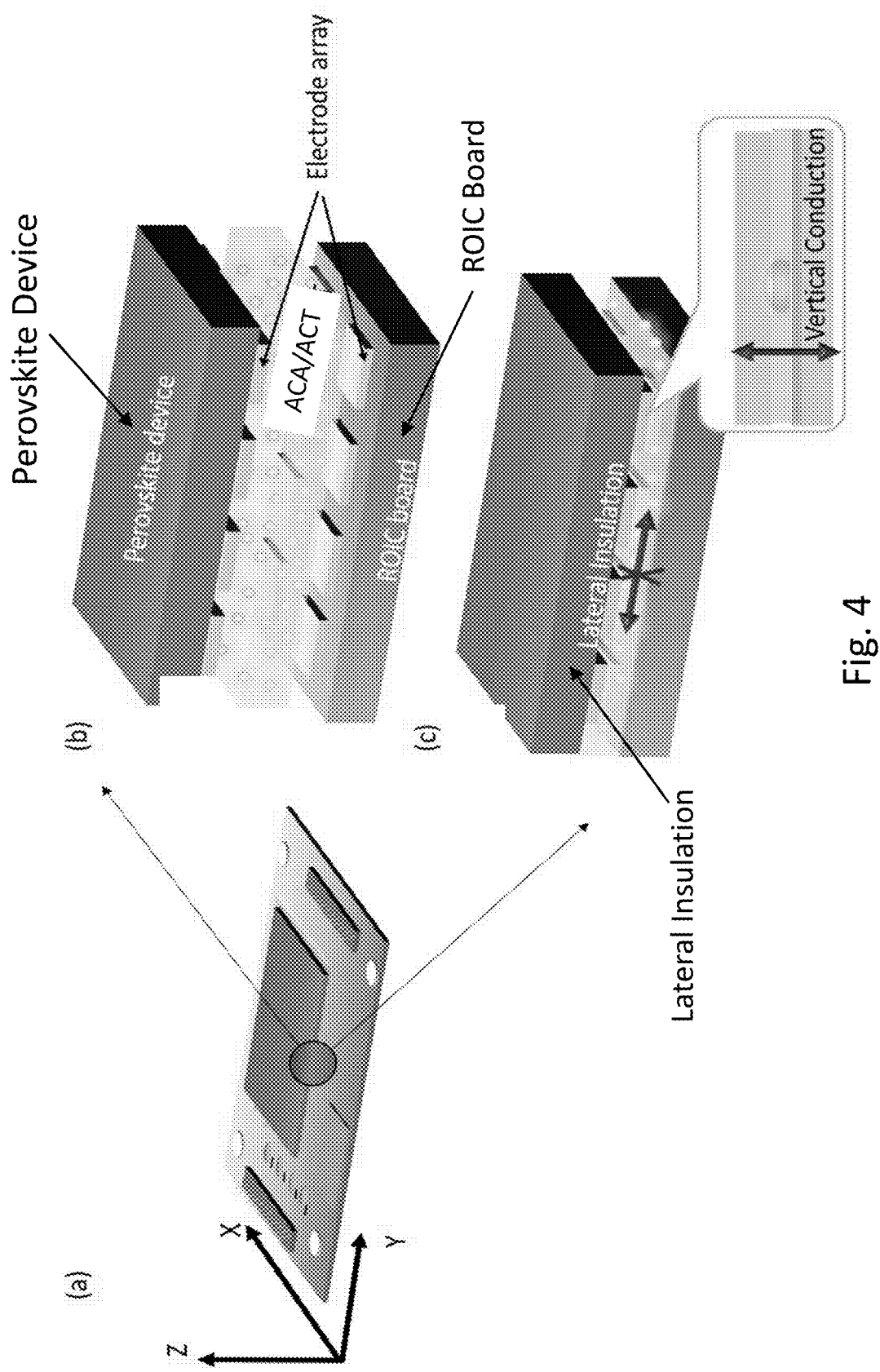
FIG. 4 shows a schematic diagram of the integration mechanism of a flexible x-ray detector on a ROIC by ACA/ACF.

The device may be directly pressed onto the readout integrated circuit (ROIC) by an anisotropic conductive adhesive (ADA) (FIG. 4), such that the anisotropic conductive adhesive is in fluid communication with the X-ray detector and the readout integrated circuit. The anisotropic conductive adhesive is an anisotropic conducting film (ACF) or anisotropic conducting paste (ACP), which includes conducting particles that are dispersed in an insulative resin composition. The anisotropic conductive adhesive is provided between objects so as to bond the objects by heating or pressing. When heated or pressed, a resin in the adhesive flows into a gap between objects so as to seal the space between electrodes facing each other disposed on the objects. Some conducting particles in the resin also flow into the space between the electrodes facing each other so as to achieve an electrical connection therebetween.

The metal particles in the ACA and ACF conduct carriers only along the Z direction (FIG. 4) and avoid the signal crosstalk of neighbor pixels at the same time, realizing digital imaging with good resolution. Without wishing to be bound by theory, the technology is based on the premise that a balanced loading and distribution of conductive particles within an adhesive matrix will allow those particles to become trapped between the upper and lower sides of an assembly, thereby conducting electricity through the vertical axis while not creating shorts in the horizontal axes.

In certain embodiments, the anisotropic conductive adhesive is an anisotropic conductive paste (ACP) or anisotropic conductive film (ACF). In certain embodiments, the anisotropic conductive adhesive is a glue. In certain embodiments, the anisotropic conductive film may be referred to as an anisotropic conductive tape (ACT). The paste form refers to a liquid form, and may contain, if required, a solvent, etc. The film form refers to an apparent film form made by application to a substrate such as a base film, etc., followed by drying.

Non-limiting examples of insulative resin compositions constituting the anisotropic conductive adhesive are epoxy-type thermosetting resin compositions. For example, resin compositions containing a curing agent and thermosetting resins such as an epoxy resin and a phenoxy resin are commonly used. The conductive particles there are dispersed in the base resin material. In certain embodiments, the conductive metal particles are selected from the group consisting of gold, nickel, aluminum, copper, chromium and silver. In certain embodiments, the anisotropic conductive adhesive is an anisotropic conductive film comprising gold particles.

In certain embodiments, the conductive particle size in the ACA or ACF does not exceed the pixel size. In certain embodiments, the distances between any two conductive particles do not exceed one period distance of pixels.

The resolution capability of the ACA or ACF may be provided by the commercial manufacturer. Both the ACAs and ACFs can be obtained with different resolutions for device integration. In certain embodiments, the ROIC has a pixel size of about 100 pixels, about 200 pixels, about 300 pixels, about 400 pixels, about 500 pixels, about 600 pixels, about 700 pixels, about 800 pixels, about 900 pixels, or about 1000 pixels.

The ROIC can be fabricated to collect electrons or holes. The array pixels of the free-standing device can be customized to extract either electrons or holes.

In certain embodiments, to achieve a stable x-ray detector, the ACA/ACF is selected based on its stability when contacted with the radiation sensitive material. It is ideal that the ACA/ACF does not react with the radiation sensitive material. In one embodiment, gold coated particles in ACF are more desirable than particles coated by silver due to the chemical reactivity of silver and the perovskite.

The subject matter described herein is directed to the following embodiments:

1. A multilayer composite film, comprising two or more layers, each layer comprising:
   i. a porous membrane comprising interconnected channels; and
   ii. a radiation sensitive material comprising a plurality of crystals,
   wherein the plurality of crystals are embedded in interconnected channels of said porous membrane;
   wherein said porous membrane and said radiation sensitive material in each adjacent layer are the same or different to those of any other layer; and said multilayer composite film is continuous.

2. The multilayer composite film of embodiment 1, wherein said crystals have a size of about 50 nanometers to about 500 micrometers.

3. The multilayer composite film of embodiment 1 or 2, wherein said radiation sensitive material comprising a plurality of crystals is selected from the group consisting of:
   a. a perovskite having a formula of $ABX_3$, wherein A is a cation selected from the group consisting of methylammonium (MA), tetramethylammonium, formamidinium (FA), cesium, rubidium, potassium, sodium, butylammonium, phenethylammonium, phenylammonium, guanidinium, ammonium, and a combination thereof; B is a metal cation selected from the group consisting of lead, tin, cadmium, germanium, zinc, nickel, platinum, palladium, mercury, titanium, silicon, and a combination thereof; and X is a halide selected from the group consisting of $Cl^-$, $Br^-$, $F^-$, $I^-$, and a combination thereof,
   b. a perovskite having a formula of $ABO_3$, wherein A is a cation selected from the group consisting of barium, magnesium, calcium, strontium, lanthanum, neodymium, praseodymium, cerium, samarium, europium, gadolinium, terbium, dysprosium, holmium, erbium, ytterbium, lutetium, and a combination thereof, B is a metal cation selected from the group consisting of silicon, titanium, iron, manganese, cobalt, nickel, aluminum, and a combination thereof, and O is oxygen;
   c. a perovskite having a formula of $A_2B'B''X_6$, wherein A is a cation selected from the group consisting of methylammonium (MA), tetramethylammonium, formamidinium (FA), cesium, rubidium, potassium, sodium, butylammonium, phenethylammonium, phenylammonium, guanidinium, ammonium, and a combination thereof; B' and B" are each independently a metal cation selected from the group consisting of lead, tin, cadmium, germanium, zinc, nickel, platinum, palladium, mercury, titanium, silicon, silver, copper, gold, calcium, bismuth, gallium, indium, antimony, and a combination thereof; and X is a halide selected from the group consisting of $Cl^-$, $Br^-$, $F^-$, $I^-$, and a combination thereof; and
   d. a material selected from the group consisting of α-Se, CsI:Tl, $HgI_2$, $PbI_2$, $Gd_2O_2S$:Tb, Cd(Zn)Te, and $(NH_4)_3Bi_2I_9$.

4. The multilayer composite film of any one of embodiments 1-3, wherein said radiation sensitive material comprising a plurality of crystals is a perovskite having the formula of $ABX_3$, wherein A is a cation selected from the group consisting of methylammonium (MA), tetramethylammonium, formamidinium (FA), cesium, rubidium, potassium, sodium, butylammonium, phenethylammonium, phenylammonium, guanidinium, ammonium, and a combination thereof; B is a metal cation selected from the group consisting of lead, tin, cadmium, germanium, zinc, nickel, platinum, palladium, mercury, titanium, silicon, and a combination thereof; and X is a halide selected from the group consisting of $Cl^-$, $Br^-$, $F^-$, $I^-$, and a combination thereof.

5. The multilayer composite film of embodiment 4, wherein said perovskite having the formula of $ABX_3$ is selected from the group consisting of $MAPbBr_3$, $MAPbI_3$, $MAPbCl_3$, and $MAPb(I_{0.9}Cl_{0.1})_3$.

6. The multilayer composite film of any one of embodiments 1-5, wherein said composite film has a thickness of about 50 nm to about 1 cm.

7. The multilayer composite film of any one of embodiments 1-6, wherein said composite film is smooth.

8. The multilayer composite film of any one of embodiments 1-7, wherein said porous membrane comprises a material selected from the group consisting of metal, ceramic, polymer, carbon, protein, and a combination thereof.

9. The multilayer composite film of embodiment 8, wherein said polymer is selected from the group consisting of nylon, low-density polyethylene (LDPE), high-density polyethylene (HDPE), polypropylene (PP), polyvinyl chloride (PVC), polyvinylidene fluoride (PVDF), polystyrene (PS), polytetrafluoroethylene (PTFE), polyimide, polyamide, polyacrilonitrile (PAN), polysulfone (PS), polyether sulfone (PES), cellulose, cellulose acetate, methyl cellulose, ethyl cellulose, nitrocellulose, hydroxylpropylcellulose (HPC), hydroxyethylcellulose (HEC), carboxymethylcellulose (CMC), polycarbonate (PCTE), polyether ether ketone (PEEK), and polydimethylsiloxane (PDMS).

10. The multilayer composite film of embodiment 9, wherein said polymer is nylon.

11. The multilayer composite film of embodiment 8, wherein said ceramic is selected from the group consisting of alumina ($Al_2O_3$), titania ($TiO_2$), zirconium oxide ($ZrO_2$), silicon carbide (SiC), silicon dioxide ($SiO_2$), spinel ($MgAl_2O_4$), mullite selected from $3Al_2O_3$-$2SiO_2$ or $2Al_2O_3$—$SiO_2$, aluminum nitride (AlN), aluminum carbide ($Al_4C_3$), silicon nitride ($Si_3N_4$), silicon carbon nitride (SiCN), silicon aluminum carbon nitride (SiAlCN), zinc oxide (ZnO), Barium titanate ($BaTiO_3$), boron oxide, boron nitride, zirconium nitride (ZrN), titanium carbide (TiC), titanium nitride (TiN), and a combination thereof.

12. The multilayer composite film of embodiment 8, wherein said metal is selected from the group consisting of Pd, Ag, Cu, Fe, Ni, W, Ti, Mo, Zn, Pt, Sn, Pb, Ga, Mg, Bi, Al, and stainless steel.

13. The multilayer composite film of embodiment 8, wherein said carbon is selected from the group consisting of carbon nanotubes (CNTs), carbon nanofibers (CNFs), carbon fiber, graphene, carbon nanohorns (CNHs), and carbon nanoparticles (CNPs).

14. The multilayer composite film of any one of embodiments 1-14, wherein said composite film is flexible.

15. The multilayer composite film of any one of embodiments 1-14, wherein said composite film comprises four layers,
   wherein Layer 1 is adjacent to Layer 2; Layer 2 is adjacent to Layer 3; and Layer 3 is adjacent to Layer 4,
   wherein said porous membrane in each of the four layers is nylon, and each layer comprises a radiation sensitive material comprising a perovskite composition having the formula of $ABX_3$, wherein the perovskite composition in each layer is:
   Layer 1: $MAPbBr_3$
   Layer 2: $MAPb(I_{0.9}Cl_{0.1})_3$
   Layer 3: $MAPb(I_{0.9}Cl_{0.1})_3$
   Layer 4: $MAPbBr_3$.

16. A composite film, comprising one layer, said layer comprising:
   i. a porous membrane comprising interconnected channels; and
   ii. a radiation sensitive material comprising a plurality of crystals,
   wherein the plurality of crystals are embedded in interconnected channels of said porous membrane; and
   wherein said composite film is continuous.

17. The composite film of embodiment 16, wherein said radiation sensitive material comprising a plurality of crystals is selected from the group consisting of:
   a. a perovskite having a formula of $ABX_3$, wherein A is a cation selected from the group consisting of methylammonium (MA), tetramethylammonium, formamidinium (FA), cesium, rubidium, potassium, sodium, butylammonium, phenethylammonium, phenylammonium, guanidinium, ammonium, and a combination thereof; B is a metal cation selected from the group consisting of lead, tin, cadmium, germanium, zinc, nickel, platinum, palladium, mercury, titanium, silicon, and a combination thereof; and X is a halide selected from the group consisting of Cl⁻, Br⁻, F⁻, I⁻, and a combination thereof,
- b. a perovskite having a formula of $ABO_3$, wherein A is a cation selected from the group consisting of barium, magnesium, calcium, strontium, lanthanum, neodymium, praseodymium, cerium, samarium, europium, gadolinium, terbium, dysprosium, holmium, erbium, ytterbium, lutetium, and a combination thereof; B is a metal cation selected from the group consisting of silicon, titanium, iron, manganese, cobalt, nickel, aluminum, and a combination thereof; and O is oxygen;
- c. a perovskite having a formula of $A_2B'B''X_6$ wherein A is a cation selected from the group consisting of methylammonium (MA), tetramethylammonium, formamidinium (FA), cesium, rubidium, potassium, sodium, butylammonium, phenethylammonium, phenylammonium, guanidinium, ammonium, and a combination thereof; B' and B" are each independently a metal cation selected from the group consisting of lead, tin, cadmium, germanium, zinc, nickel, platinum, palladium, mercury, titanium, silicon, silver, copper, gold, calcium, bismuth, gallium, indium, antimony, and a combination thereof; and X is a halide selected from the group consisting of Cl⁻, Br⁻, F⁻, I⁻, and a combination thereof; and
- d. a material selected from the group consisting of α-Se, CsI:Tl, $HgI_2$, $PbI_2$, $Gd_2O_2S:Tb$, Cd(Zn)Te, and $(NH_4)_3Bi_2I_9$.

18. The composite film of embodiment 17, wherein said radiation sensitive material comprising a plurality of crystals is a perovskite having the formula of $ABX_3$, where A is a cation selected from the group consisting of methylammonium (MA), tetramethylammonium, formamidinium (FA), cesium, rubidium, potassium, sodium, butylammonium, phenethylammonium, phenylammonium, guanidinium, ammonium, and a combination thereof; B is a metal cation selected from the group consisting of lead, tin, cadmium, germanium, zinc, nickel, platinum, palladium, mercury, titanium, silicon, and a combination thereof; and X is a halide selected from the group consisting of Cl⁻, Br⁻, F⁻, I⁻, and a combination thereof.

19. The composite film of any one of embodiments 16-18, wherein said composite film is smooth.

20. The composite film of any one of embodiments 16-19, wherein said porous membrane comprises a material selected from the group consisting of metal, ceramic, polymer, carbon, protein, and a combination thereof.

21. The composite film of embodiment 20, wherein said polymer is selected from the group consisting of nylon, low-density polyethylene (LDPE), high-density polyethylene (HDPE), polypropylene (PP), polyvinyl chloride (PVC), polyvinylidene fluoride (PVDF), polystyrene (PS), polytetrafluoroethylene (PTFE), polyimide, polyamide, polyacrilonitrile (PAN), polysulfone (PS), polyether sulfone (PES), cellulose, cellulose acetate, methyl cellulose, ethyl cellulose, nitrocellulose, hydroxylpropylcellulose (HPC), hydroxyethylcellulose (HEC), carboxymethylcellulose (CMC), polycarbonate (PCTE), polyether ether ketone (PEEK), and polydimethylsiloxane (PDMS).

22. The composite film of embodiment 20 or 21, wherein said polymer is nylon.

23. The composite film of any one of embodiments 16-22, wherein said porous membrane is nylon and said radiation sensitive material is a perovskite composition having a formula of $MAPb(I_{0.9}Cl_{0.1})_3$.

24. An X-ray device comprising the multilayer composite film of any one of embodiments 1-15 or the composite film of any one of embodiments 16-23, and an electrode.

25. The X-ray device of embodiment 24, wherein said composite film is a photoactive layer in said device and said X-ray device is an X-ray detector.

26. An X-ray detector comprising the multilayer composite film of any one of embodiments 1-15 or the composite film of any one of embodiments 16-23, an optional first transport layer, a second transport layer, a first electrode, and a second electrode, wherein said first transport layer, if present, is disposed on said first electrode, said composite film is disposed on said first transport layer if present, said second transport layer is disposed on said composite film, and said second electrode is disposed on said second transport layer.

26A. The X-ray detector of embodiment 26, wherein when said first transport layer is not present, said composite film is disposed on said first electrode, said second transport layer is disposed on said composite film, and said second electrode is disposed on said second transport layer.

26B. An X-ray detector comprising the multilayer composite film of any one of embodiments 1-15 or the composite film of any one of embodiments 16-23, a first transport layer, a second transport layer, a first electrode, and a second electrode, wherein said first transport layer is disposed on said first electrode, said composite film is disposed on said first transport layer, said second transport layer is disposed on said composite film, and said second electrode is disposed on said second transport layer.

27. The X-ray detector of embodiment 26, wherein said detector is flexible.

28. A method of preparing an integrated X-ray detector for use in digital X-ray imaging, said method comprising contacting an anisotropic conductive adhesive with a readout integrated circuit and contacting said anisotropic conductive adhesive with said X-ray detector of embodiment 26.

29. The method of embodiment 28, wherein said anisotropic conductive adhesive is an anisotropic conductive paste or an anisotropic conductive film.

30. The method of embodiment 29, wherein said anisotropic conductive film comprises conductive particles selected from the group consisting of gold, nickel, aluminum, copper, chromium and silver.

31. The method of embodiment 30, wherein said anisotropic conductive film comprises gold particles.

32. The X-ray detector of any one of embodiments 26-30, for use in digital X-ray imaging, wherein said X-ray detector further comprises an anisotropic conductive adhesive and a readout integrated circuit, wherein said anisotropic conductive adhesive is in fluid communication with said detector and said readout integrated circuit.

33. A method of preparing a multilayer continuous composite film comprising two or more layers, said method comprising:
- a) passing a radiation sensitive material precursor solution through a porous membrane, wherein one or more crystals of the radiation sensitive material are retained in one or more pores of said porous membrane;

wherein a) is carried out two or more times to prepare said two or more layers; wherein said radiation sensitive material precursor solution and said porous membrane in adjacent layers are the same or different; and b) compressing said two or more layers to prepare said continuous composite film.

34. A method of preparing a continuous composite film comprising one layer, said method comprising:
a) passing a radiation sensitive material precursor solution through a porous membrane, wherein one or more crystals of the radiation sensitive material are retained in one or more pores of said porous membrane; and
b) compressing said layer to prepare said continuous composite film.

35. A method for preparing a continuous composite film comprising one or more layers, said method comprising:
a) contacting a radiation sensitive material with a porous membrane;
b) applying a temperature and pressure effective enough to melt said radiation sensitive material, producing a melted material;
c) contacting said melted material with pores of said membrane; and
d) cooling said membrane to prepare a membrane with solidified radiation sensitive material embedded in pores of said membrane.
wherein a)-d) are carried out one or more times to prepare said one or more layers; wherein said radiation sensitive material and said porous membrane in adjacent layers are the same or different; and
e) compressing said one or more layers to prepare said continuous composite film.

36. A method of preparing a continuous multilayer composite film comprising two or more layers, said method comprising:
passing a radiation sensitive material precursor solution through two or more porous membranes, wherein one or more crystals of the radiation sensitive material are retained in one or more pores of said porous membranes;
wherein said porous membranes in adjacent layers are each the same or different; and compressing said two or more layers to prepare said continuous composite film.

37. A method of preparing a continuous multilayer composite film comprising a four-layer composition, wherein Layer 1 is adjacent to Layer 2; Layer 2 is adjacent to Layer 3; and Layer 3 is adjacent to Layer 4, said method comprising:
passing a MAPbBr$_3$ solution through a first porous membrane, wherein one or more crystals of the MAPbBr$_3$ solution are retained in one or more pores of said first porous membrane to prepare Layer 1,
passing a MAPb(I$_{0.9}$Cl$_{0.1}$)$_3$ solution through a second porous membrane, wherein one or more crystals of the MAPb(I$_{0.9}$Cl$_{0.1}$)$_3$ solution are retained in one or more pores of said second porous membrane to prepare Layer 2;
passing a MAPb(I$_{0.9}$Cl$_{0.1}$)$_3$ solution through a third porous membrane, wherein one or more crystals of the MAPb(I$_{0.9}$Cl$_{0.1}$)$_3$ solution are retained in one or more pores of said third porous membrane to prepare Layer 3;
passing a MAPbBr$_3$ solution through a fourth porous membrane, wherein one or more crystals of the MAPbBr$_3$ solution are retained in one or more pores of said fourth porous membrane to prepare Layer 4,
wherein each of said first, second, third, and fourth porous membranes is nylon;
compressing said four-layer composition for about 90 s, at a temperature of about 308 K, and a pressure of about 0.5 MPa, followed by a pressure of about 2 MPa, at a temperature of about 473.15 K, for about 120 s to prepare said continuous composite film.

38. A method of preparing a continuous multilayer composite film comprising a four-layer composition, wherein Layer 1 is adjacent to Layer 2; Layer 2 is adjacent to Layer 3; and Layer 3 is adjacent to Layer 4, said method comprising:
passing a MAPb(I$_{0.9}$Cl$_{0.1}$)$_3$ solution through two porous membranes, wherein one or more crystals of the MAPb(I$_{0.9}$Cl$_{0.1}$)$_3$ solution are retained in one or more pores of said porous membranes to prepare Layer 2 and Layer 3;
passing a MAPbBr$_3$ solution through two porous membranes, wherein one or more crystals of the MAPbBr$_3$ solution are retained in one or more pores of said porous membranes to prepare Layer 1 and Layer 4,
wherein each of said porous membranes is nylon;
compressing said four-layer composition for about 90 s, at a temperature of about 308 K, and a pressure of about 0.5 MPa, followed by a pressure of about 2 MPa, at a temperature of about 473.15 K, for about 120 s, to prepare said continuous composite film.

39. The method of any one of embodiments 33-38, wherein said continuous composite film is flexible.

40. The method of any one of embodiments 33-39, wherein compressing comprises applying a pressure and a temperature to said two or more layers.

41. The method of embodiment 40, wherein said temperature is at least 290 K.

42. The method of any one of embodiments 33-41, wherein said passing further comprises applying a pressure difference between two sides of said membrane.

43. The method of any one of embodiments 33-42, wherein said porous membrane is immersed in said radiation sensitive material precursor solution prior to said passing.

44. The method of any one of embodiments 33-43, wherein a) further comprises annealing said membrane.

45. The method of any one of embodiments 33-44, wherein said radiation sensitive material precursor solution is a perovskite precursor solution.

46. The method of embodiment 45, wherein said perovskite precursor solution comprises a composition of formula (I):

$$ABX_3 \qquad (I)$$

wherein A is a cation selected from the group consisting of methylammonium, tetramethylammonium, formamidinium, cesium, rubidium, potassium, sodium, butylammonium, phenethylammonium, phenylammonium, guanidinium, ammonium, and a combination thereof,
B is a metal cation selected from the group consisting of lead, tin, cadmium, germanium, zinc, nickel, platinum, palladium, mercury, titanium, silicon, and a combination thereof, and
X is a halide selected from the group consisting of Cl$^-$, Br$^-$, F$^-$, I$^-$, and a combination thereof; and
one or more solvents selected from the group consisting of dimethyl sulfoxide, dimethylformamide, γ-butyrolactone, 2-methoxyethanol, and acetonitrile.

47. The method of embodiment 46, wherein said perovskite precursor solution further comprises a compound of formula AX, wherein A is at least one monovalent cation selected from the group consisting of methylammonium, tetramethylammonium, formamidinium, guanidinium, cesium, rubidium, potassium, sodium, butylammonium, phenethylammonium, ammonium, and phenylammonium; and X is selected from the group consisting of Br$^-$, Cl$^-$, I$^-$, acetate (CH$_3$CO$_2^-$), and thiocyanate (SCN$^-$).

48. The method of embodiment 47, wherein said compound of formula AX is present in said perovskite precursor solution in about a 10% molar ratio.

49. The method of embodiment 47 or 48, wherein A is methylammonium, B is lead, X is (I$_{0.9}$Cl$_{0.3}$)$_3$, said one or more solvents is 2-methoxyethanol, and said formula of AX is methylammonium chloride.

50. The method of any one of embodiments 33-49, wherein said porous membrane has an average pore size of about 10 nm to about 1 mm.

51. The method of embodiments 33-50, wherein said porous membrane has a thickness of about 10 µm to about 10 cm.

52. The method of any one of embodiments 33-51, wherein the thickness of the continuous composite film produced is about 10 nm to about 1 cm.

53. The method of any one of embodiments 33-52, wherein said porous membrane comprises a material selected from the group consisting of metal, ceramic, polymer, carbon, protein, and a combination thereof.

54. The method of embodiment 53, wherein said polymer is selected from the group consisting of nylon, low-density polyethylene (LDPE), high-density polyethylene (HDPE), polypropylene (PP), polyvinyl chloride (PVC), polyvinylidene fluoride (PVDF), polystyrene (PS), polytetrafluoroethylene (PTFE), polyimide, polyamide, polyacrilonitrile (PAN), polysulfone (PS), polyether sulfone (PES), cellulose, cellulose acetate, methyl cellulose, ethyl cellulose, nitrocellulose, hydroxylpropylcellulose (HPC), hydroxyethylcellulose (HEC), carboxymethylcellulose (CMC), polycarbonate (PCTE), polyether ether ketone (PEEK), and polydimethylsiloxane (PDMS).

55. The method of embodiment 54, wherein said polymer is nylon.

56. The method of any one of embodiments 33-55, wherein said continuous composite film comprises four layers, wherein Layer 1 is adjacent to Layer 2; Layer 2 is adjacent to Layer 3; and Layer 3 is adjacent to Layer 4, wherein said porous membrane in each of the four layers is nylon, and each layer comprises a radiation sensitive material comprising a perovskite composition having the formula of ABX$_3$, wherein the perovskite composition in each layer is:

Layer 1: MAPbBr$_3$
Layer 2: MAPb(I$_{0.9}$Cl$_{0.1}$)$_3$
Layer 3: MAPb(I$_{0.9}$Cl$_{0.1}$)$_3$
Layer 4: MAPbBr$_3$.

57. The method of embodiment 34, wherein said porous membrane is nylon and said radiation sensitive material is a perovskite composition having a formula of MAPb(I$_{0.9}$Cl$_{0.1}$)$_3$.

58. The method of embodiments 33-57, wherein said radiation sensitive crystals have a size of about 50 nanometers to about 500 micrometers.

59. The method of embodiment 42, wherein said pressure is between about 0.1 MPa and about 10 GPa.

60. The X-ray detector of any one of embodiments 26, 26A, or 26B, wherein said detector has a µτ of about $1.5 \times 10^{-3}$ cm$^2$V$^{-1}$.

61. The X-ray detector of embodiment 26, wherein said detector exhibits a sensitivity of about 1000 to about 3800 µC Gy$_{air}^{-1}$ cm$^{-2}$ under a bias of 0.05 V/µm.

62. The X-ray detector of embodiment 26, wherein said detector exhibits a sensitivity of about 2678 µC Gy$_{air}^{-1}$ cm$^{-2}$ under a bias of 0.05 V/µm.

63. The X-ray detector of embodiment 26, wherein said detector has a thickness of about 10 nm to about 1 cm.

64. The X-ray detector of embodiment 63, wherein said detector has a thickness of about 90 µm to about 500 µm.

65. The X-ray detector of embodiment 64, wherein said detector has a thickness selected from the group consisting of 130 µm, 220 µm, 260 µm, and 380 µm.

66. The method of any one of embodiments 33-59, wherein said continuous composite film has a density of about 1 g/cm$^3$ to about 7 g/cm$^3$.

67. The multilayer composite film of any one of embodiments 1-15, wherein said film has a density of about 1 g/cm$^3$ to about 7 g/cm$^3$.

68. The composite film of any one of embodiments 16-23, wherein said film has a density of about 1 g/cm$^3$ to about 7 g/cm$^3$.

The following examples are offered by way of illustration and not by way of limitation.

EXAMPLES

Example 1: Perovskite Precursor Solution Preparation for Materials Filling

Figure 1C:
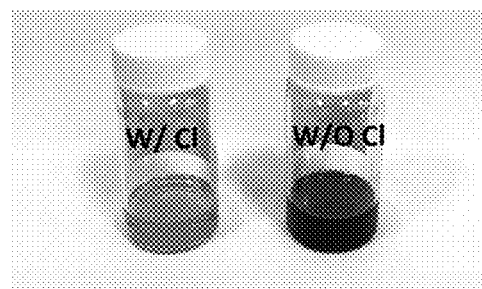
FIG. 1C shows a picture of 3M perovskite precursor solutions with MACl and without MACl mixing.
Figure 1D:
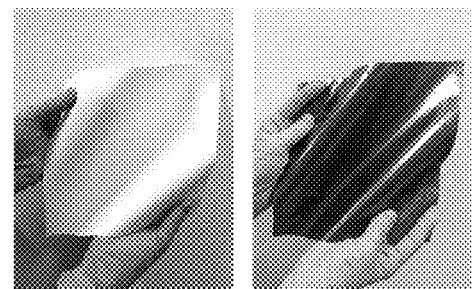
FIG. 1D shows a picture of a large area (20*20 cm$^2$) flexible membrane before and after perovskite filling.

A saturated perovskite precursor solution can be prepared up to 3 M by mixing in a 10% molar ratio of MACl. As shown in FIG. 1C, without the presence of MACl mixed into the solution, the precursor solution was not clear. This lack of clarity is indicative of perovskite crystals precipitating from the precursor solution. As such, the MAPb(I$_{0.9}$Cl$_{0.1}$)$_3$/2ME saturated precursor solution was prepared with a high concentration, so as to promote the high filling ratio of perovskite microcrystals in the membrane.

It was additionally discovered that the solubility of the perovskite in 2ME increased when the temperature decreased. Without wishing to be bound by theory, it is understood that if the precursor solution were prepared at lower temperatures, the saturated precursor solution could exceed 3M (prepared under room temperature), and the filling ratio of the perovskite in the membrane could also increase.

Example 2: Dark Current and EDS of Stacked Perovskite Filled Membranes

Figure 2B:
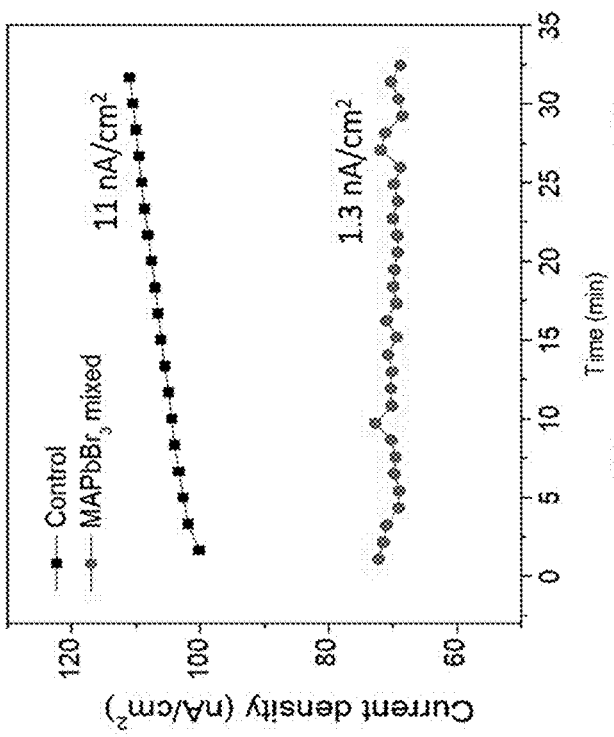
FIG. 2B shows dark current stability of a control device and a MAPbBr$_3$ mixed device.
Figure 2A:
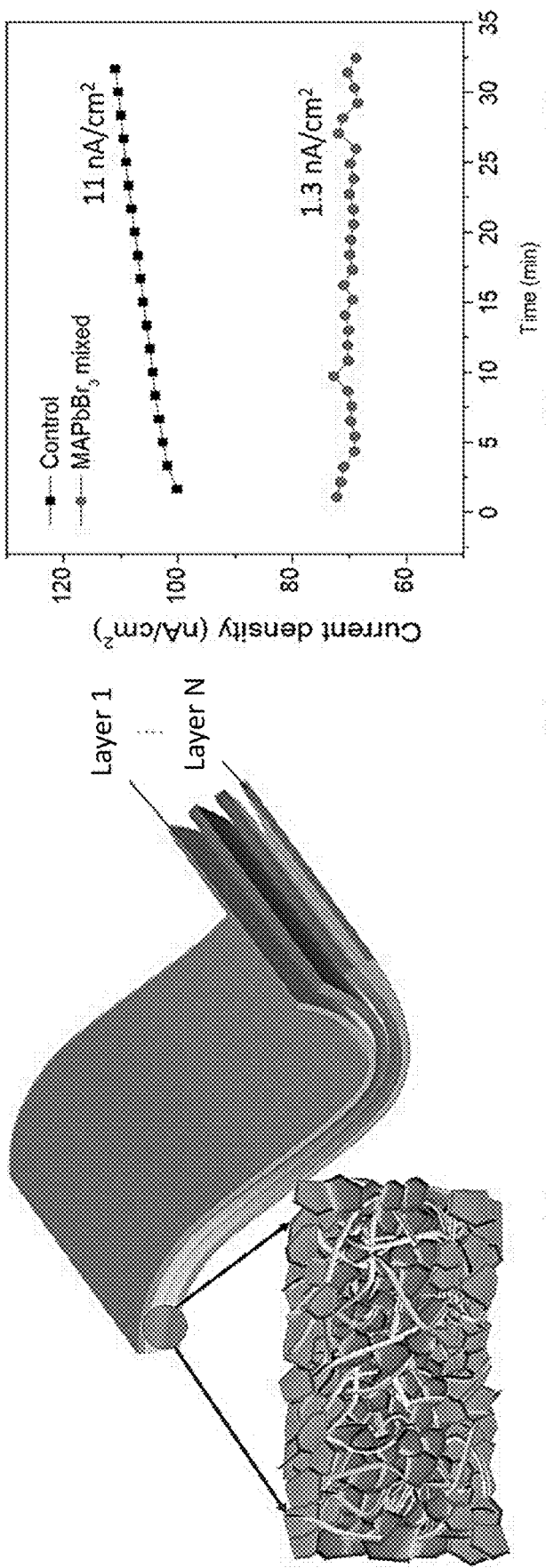
FIG. 2A shows a diagram of stacking perovskite-filled membranes for x-ray imaging.
Figure 2D:
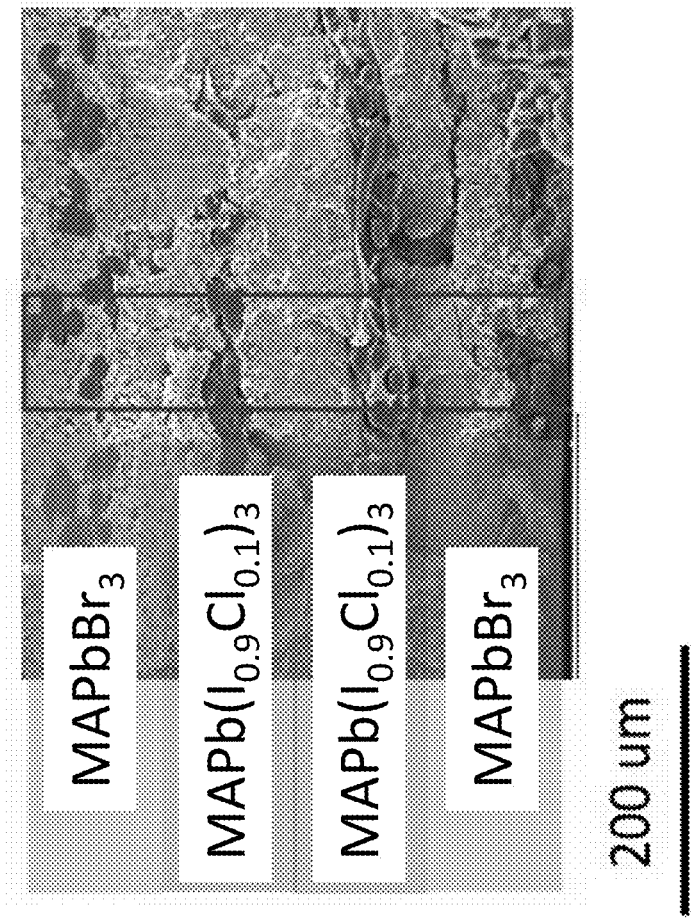
FIG. 2D shows a SEM of the cross section of the MAPbBr$_3$ mixed device
Figure 2C:
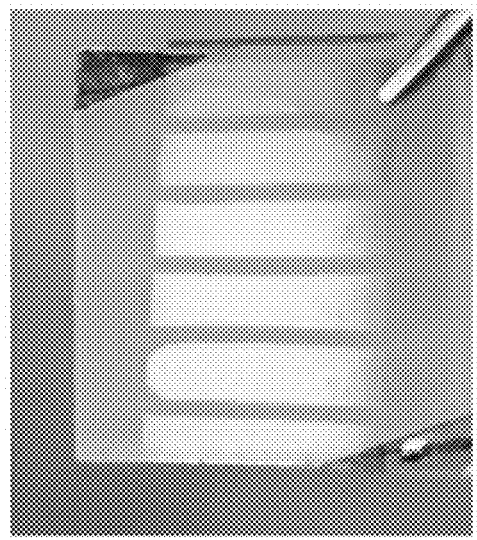
FIG. 2C shows a picture of the MAPbBr$_3$ mixed device.
Figures 2E, 2F, 2G:
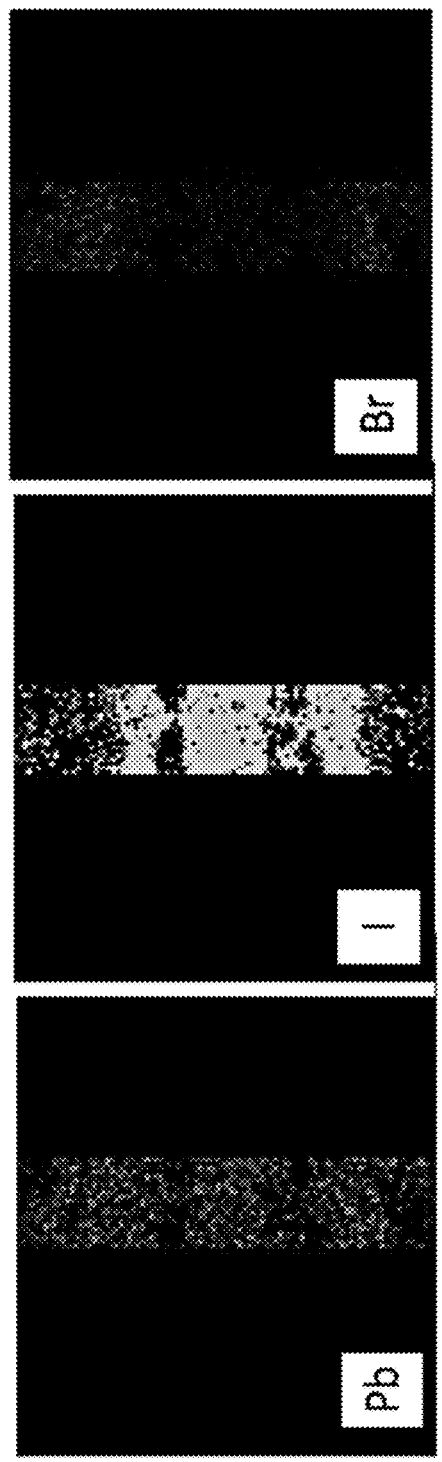
FIG. 2E shows EDS mapping, exhibiting Pb signal.
FIG. 2F shows EDS mapping, exhibiting I signal.
FIG. 2G shows EDS mapping, exhibiting Br signal.

A device based on the structure of MAPbBr$_3$/MAPb (I$_{0.9}$Cl$_{0.1}$)$_3$/MAPb(I$_{0.9}$Cl$_{0.1}$)$_3$/MAPbBr$_3$ mixed multilayer perovskite membrane was fabricated (FIG. 2C). A device based on pure MAPb(I$_{0.9}$Cl$_{0.1}$)$_3$ perovskite membranes was also prepared as a control. As shown in FIG. 2B, under the same bias, the current drift for the MAPbBr$_3$ mixed device was only 1.3 nA/cm$^2$, while the control device exhibited a larger dark current drift of 11 nA/cm$^2$. In FIG. 2E through FIG. 2G, the energy dispersive spectroscopy (EDS) of the cross-section of the MAPbBr$_3$ mixed device in the pink rectangular area was measured. The Br signal clearly showed on the top and bottom, while the I signal appeared in the middle. The Pb signal was uniformly distributed through the whole cross section.

Example 3: Compressing Process

Compressing was applied to enhance membrane density. Compressing was conducted at 35° C., 90 s, 0.5 MPa and 200° C., 120 s, 2 MPa. Two glass slides with flat, smooth surfaces were used as templates to press the membrane for flattening the membrane surfaces after hot pressing. After the glass slides were treated by Ozone plasma, they were doctor-bladed with a hydrophobic material, (trichloro(3 3 3-trifluoropropyl)silane/toluene 1:20 Volume ratio), and annealed at 100° C. for 1 min to dry the hydrophobic material layer. Then, the saturated MAI/IPA (MAI=methylammonium iodide; IPA=isopropanol) solution was doctor bladed on top of the slide and annealed at 100° C. for 1 min to allow evaporation of the IPA. After compressing, the hydrophobic material helped to prevent the perovskite from attaching to the glass slides. However, during the hot pressing process, it was possible for the perovskite to degrade by producing $PbI_2$, losing MAI. Thus, the MAI layer on the glass slides helped suppress and/or compensate for the lost MAI during the compressing process.

Figure 3E:
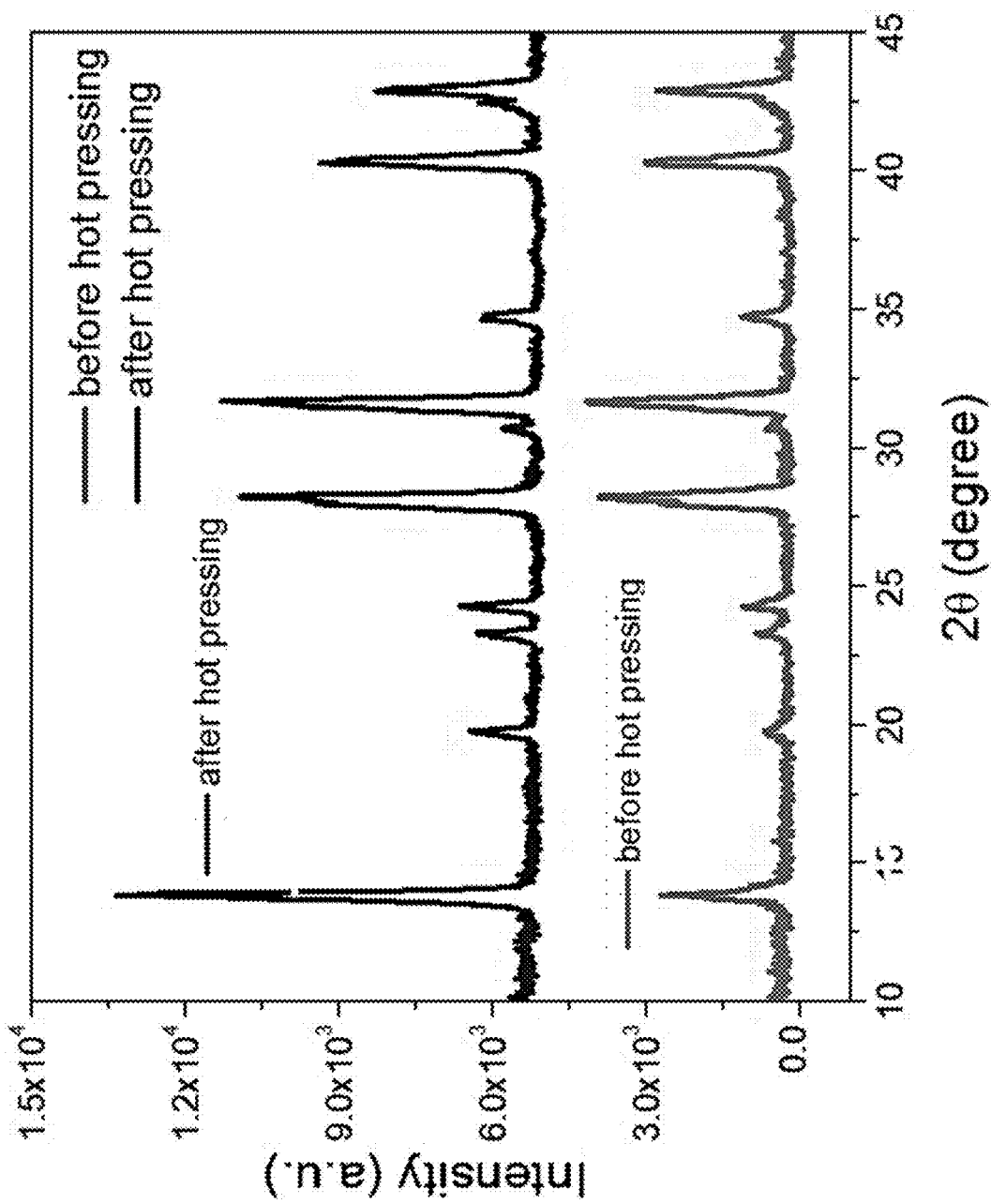
FIG. 3E shows x-ray diffraction patterns of the perovskite filled membrane before and after hot pressing.

It can be seen that the rough, loose perovskite filled-membrane became smooth, dense, compact, and continuous after compressing, as shown in FIG. 3A and FIG. 3B. The loose structure before compressing benefited from solvent evaporation during thermal annealing. It is understood that the compact layer has improved density after compressing, thereby enhancing its X-ray attenuation and carrier transport. The rough surfaces before compressing could cause issues such as non-continuous common electrodes and large dark current, which were eliminated in the hot-pressed membrane. In addition, as shown in FIG. 3E, the crystallinity of the perovskite filled membrane was also enhanced following compressing. It can be understood that the perovskite benefitted from the coarsening process of the perovskite microcrystals during hot pressing. Depending on the applications, the X-ray detector can be fabricated to different thicknesses by compressing different layers of perovskite-filled membranes and engineered to different compositions by modifying the composition of perovskite in each layer.

Example 4: Evaluation of X-Ray Detector Physical Properties

A low cost, lightweight, durable, highly sensitive and flexible X-ray detector with a customizable thickness and composition was fabricated. A nylon membrane with a pore size of 5 µm and a thickness of ~100 µm was used to fabricate the flexible devices. It is typically desirable for X-ray detectors to have a high µτ product (mobility-lifetime product) to achieve effective charge collection in thick bulk materials. The composition of the perovskite x-ray detector was engineered bearing this in mind. The µτ product of the perovskite film was enhanced by mixing a 10% molar ratio of MACl with $MAPbI_3$. A 3 M $MAPb(I_{0.9}Cl_{0.1})_3$/2ME precursor solution was used for filling the nylon membrane and a structure of $Cr/MAPb(I_{0.9}Cl_{0.1})_3/C_{60}/BCP/Cr$ was fabricated. The µτ product was measured using a photoconductivity method and fitted to the following modified Hecht equation:

$$I = \frac{I_0 \mu \tau V}{L^2} \frac{1 - \exp\left(-\frac{L^2}{\mu \tau V}\right)}{1 + \frac{L}{V}\frac{2}{\mu}},$$

where $I_0$ is the saturated photocurrent, L is the thickness of the device, and V is the applied bias. The µτ product of the device was determined to be $1.5*10^{-3}$ cm$^2$V$^{-1}$.

Figure 5A:
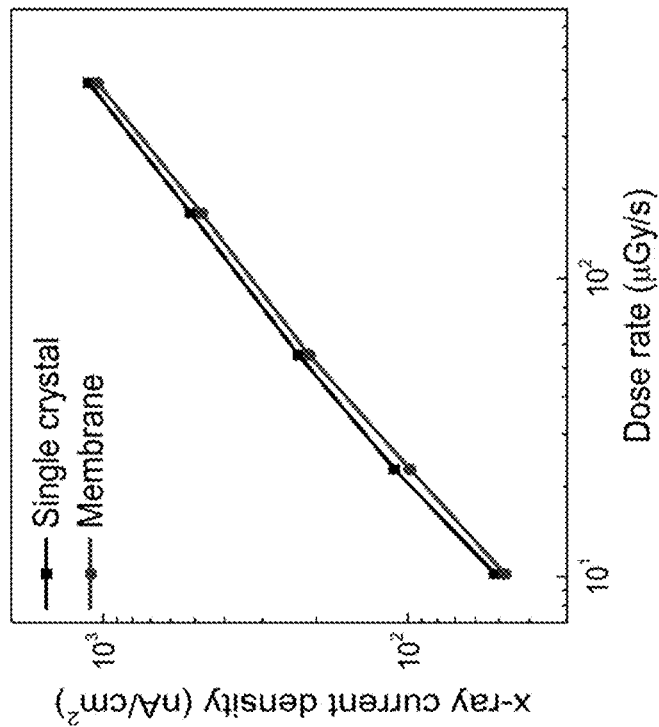
FIG. 5A shows the photoconductivity of the perovskite filled membrane device.
Figure 5B:
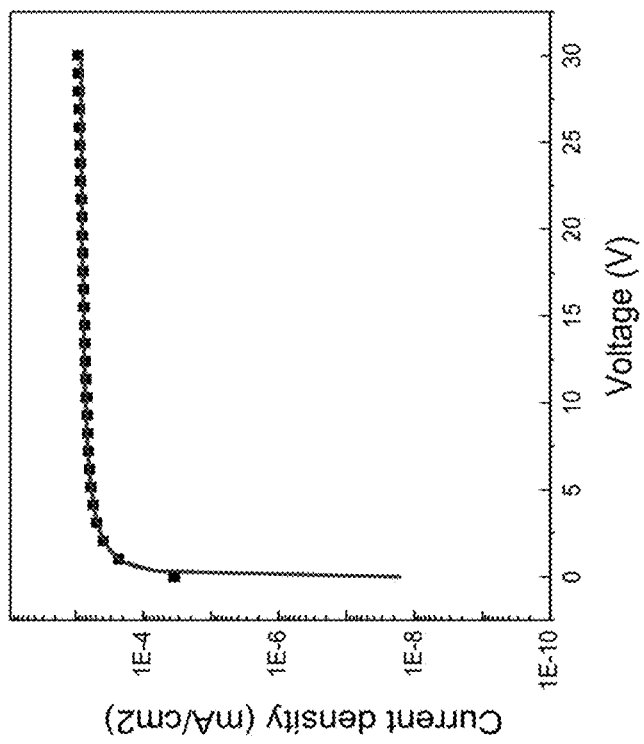
FIG. 5B shows the sensitivity of MAPbBr$_3$ single crystal and MAPb(I$_{0.9}$Cl$_{0.1}$)$_3$ perovskite filled membrane device.

The sensitivity of the 220 µm thick membrane device was around 2678 µC Gy$_{air}^{-1}$ cm$^{-2}$ under a bias of 0.05 V/µm, which is comparable to that of $MAPbBr_3$ single crystal devices (2897 µC Gy$_{air}^{-1}$ cm$^{-2}$) under the same bias, as shown in FIG. 5B. The x-ray sensitivity of the devices was calculated using the slope of the device x-ray current density versus x-ray dose rate.[8,17] In FIG. 5C, devices with thicknesses of 130 µm, 260 µm, and 380 µm exhibited sensitivities of 1030, 2611, and 3758 µC Gy$_{air}^{-1}$ cm$^{-2}$, respectively, under a 0.05 V/µm bias. The dark current of the device under a 0.05 V/µm bias was stable. Under the application of a higher bias, the sensitivity increased. However, it is generally accepted that under the application of a high bias, the dark current may tend to drift.[10]

Figure 5D:
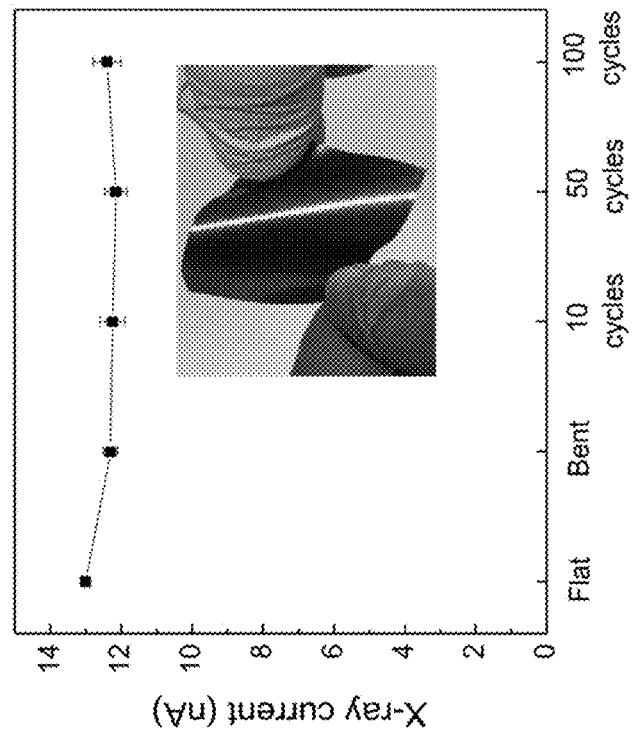
FIG. 5D shows the bendability of the 220 μm thick device. In the inset is a picture of the perovskite-filled membrane.
Figure 5C:
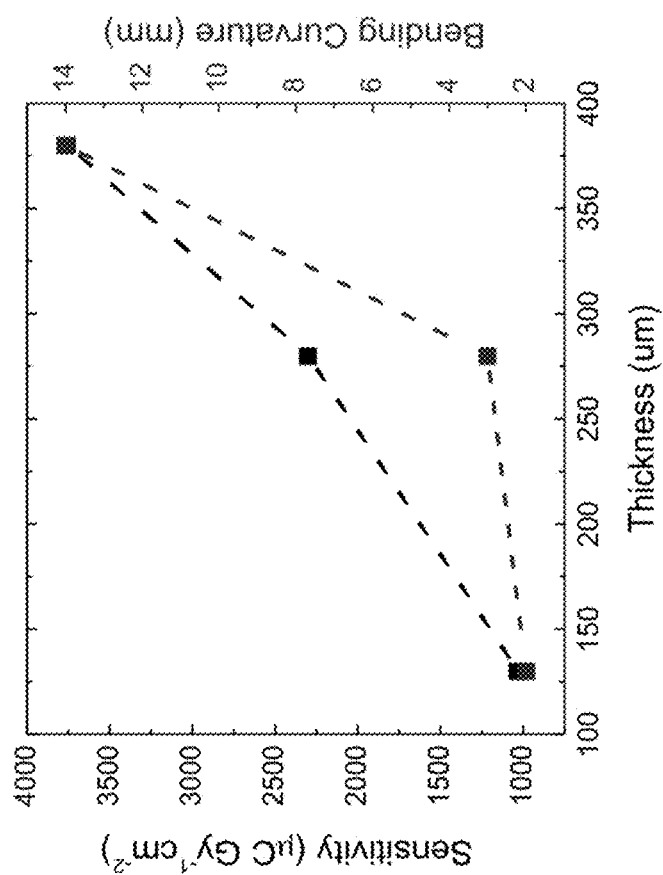
FIG. 5C shows the sensitivity and flexibility of the device with different thicknesses.

With high sensitivity, the device still sustained good flexibility. As shown in FIG. 5D, the x-ray response of a 220 µm thick device almost did not change while in a bending state and after bending for 100 cycles with 3 mm curvature. The flexibility of the devices with different thicknesses was also investigated, as shown in FIG. 5C. The devices with thicknesses of 130 µm, 260 µm, and 380 µm could sustain their photocurrent when the device was bent to a curvature with a radius of 2 mm, 3 mm, and 14 mm.

Figure 6B:
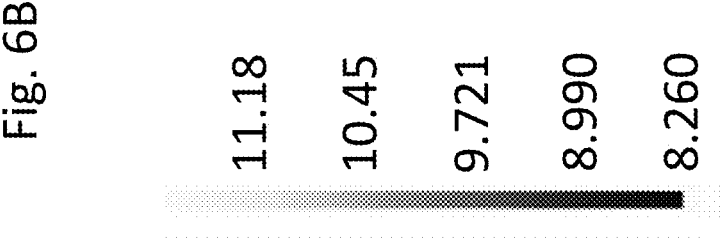
FIG. 6B shows the X-ray current intensity of linear pixels on a perovskite membrane under a bending state.
Figure 6A:
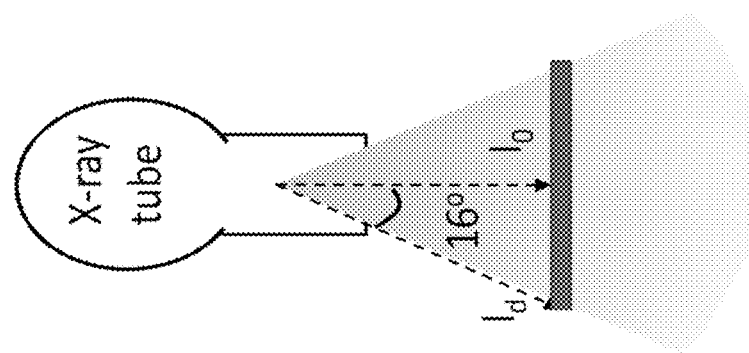
FIG. 6A shows the X-ray current intensity of linear pixels on a perovskite membrane under a flat state.

Due to the inverse square law and tilted incident angle, flat X-ray detectors commonly suffer from vignetting problems. Although several methods have been put forth to deal with the non-uniformity, such as adding compensation filtering, increasing the source detector distance, and adjusting the hardware/software, these methods could attenuate the X-ray dose, causing magnification problems and limiting the detector setup to only one configuration. However, it was discovered that the vignetting issues could be naturally eliminated by applying flexible X-ray detectors with curved surfaces, which was conceptually verified by bending one membrane with linear pixels. The X-ray had a half divergence angle of 16°. As shown in FIG. 6A, the membrane was in a flat state for the control sample. In the experimental sample (and FIG. 6B), the same membrane was bent to compensate for the X-ray path and its angle was tilted. The X-ray current intensity was scaled with a color bar for intuitive observation. For the control sample, the color was bright for the central pixel and became darker for the devices closer to the edge, which was caused by the longer X-ray pathway and titled angle to the edge detector, resulting in lower X-ray current for the edge pixels. However, the X-ray current intensity of pixels was more uniform for the membrane in the bending state.

Without sacrificing any X-ray intensity, the vignetting problem was solved. Thus, misdiagnosis and errors in screening can be avoided by using the application herein. Furthermore, unlike commercial curve detectors, which are fixed in one configuration, this flexible x-ray detector can be applied to different X-ray imaging configurations depending on different situations.

Example 5: Imaging Capability Investigations

The imaging capability of the flexible device was analyzed using a 220 µm thick single pixel free standing device under 60 KeV and 8 KeV X-rays. Objects were scanned in xy directions above the detector, which had a pixel size of 200 µm. A razor blade and Pb test phantom were used for the x-ray imaging investigations. As shown in FIG. 7A and FIG. 7B, the X-ray imaging of the razor blade and Pb test phantom can be clearly seen.

The imaging capability of the integrated X-ray detector is shown in FIG. 8B. A perovskite filled membrane device with the structure, Cr/perovskite/C60/BCP/Cr, was integrated on a commercial ROIC, which had 600 (20*30) pixels and a pixel size of 2 mm by ACF (FIG. 8A). Under a 0.16 s pulse exposure of a 60 kV X-ray, the logo "HUANG" was clearly digitally imaged by the integrated X-ray detector. The flexible X-ray detector could also conform into a narrow space, such as a pipe. As shown in FIG. 8C, a pipe with a cross hole was used for evaluating the performance of the flexible X-ray detector. A free-standing device with linear pixels was connected to the readout system. The flexible device was set inside of the pipe and scanned in one direction. The cross hole was clearly imaged. While the pipe was imaged by the detector outside, the hole could not be distinguished from the background signals. It is understood that a higher X-ray energy (>100 KeV) could enable X-rays to penetrate thick pipes for imaging. By imaging with a flexible x-ray detector with low energy x-rays, however, a higher resolution can be obtained.

REFERENCES

The references listed below as well as all references cited in the specification are incorporated herein by reference to the extent that they supplement, explain, provide a background for or teach methodology, techniques and/or compositions employed herein. All cited patents and publications referred to in this application are herein expressly incorporated by reference.

1. Kasap, S. et al. Amorphous and polycrystalline photoconductors for direct conversion flat panel X-ray image sensors. *Sensors* 11, 5112-5157 (2011).
2. Nagarkar, V. et al. Structured CsI (Tl) scintillators for X-ray imaging applications. *IEEE transactions on nuclear science* 45, 492-496 (1998).
3. Zentai, G., Schieber, M., Partain, L., Pavlyuchkova, R. & Proano, C. Large area mercuric iodide and lead iodide X-ray detectors for medical and non-destructive industrial imaging. *Journal of Crystal Growth* 275, e1327-e1331 (2005).
4. Street, R. et al. Comparison of PbI 2 and HgI 2 for direct detection active matrix x-ray image sensors. *Journal of Applied Physics* 91, 3345-3355 (2002).
5. Yun, S., Han, J. C., Ko, J. S., Kim, Y. S. & Kim, H. K. Characterization of imaging performances of gadolinium-oxysulfide phosphors made for x-ray imaging by using a sedimentation process. *Journal of the Korean Physical Society* 60, 514-520 (2012).
6. Szeles, C. CdZnTe and CdTe materials for X-ray and gamma ray radiation detector applications. *physica status solidi (b)* 241, 783-790 (2004).
7. Morse, T. F. et al. in *Radiation Detectors in Medicine, Industry, and National Security XIX* 107630C (International Society for Optics and Photonics).
8. Wei, W. et al. Monolithic integration of hybrid perovskite single crystals with heterogenous substrate for highly sensitive X-ray imaging. *Nature Photonics* 11, 315 (2017).
9. Kim, Y. C. et al. Printable organometallic perovskite enables large-area, low-dose X-ray imaging. *Nature* 550, 87-91 (2017).
10. Shrestha, S. et al. High-performance direct conversion X-ray detectors based on sintered hybrid lead triiodide perovskite wafers. *Nature Photonics* 11, 436 (2017).
11. Basirico, L. et al. Direct X-ray photoconversion in flexible organic thin film devices operated below 1 V. *Nature communications* 7, 13063 (2016).
12. Gelinck, G. H. et al. X-ray detector-on-plastic with high sensitivity using low cost, solution-processed organic photodiodes. *IEEE Transactions on Electron Devices* 63, 197-204 (2016).
13. Kuo, T.-T. et al. Flexible x-ray imaging detector based on direct conversion in amorphous selenium. *Journal of Vacuum Science & Technology A: Vacuum, Surfaces, and Films* 32, 041507 (2014).
14. Marrs, M. A. & Raupp, G. B. Substrate and Passivation Techniques for Flexible Amorphous Silicon-Based X-ray Detectors. *Sensors* 16, 1162 (2016).
15. Gill, H. S. et al. Flexible perovskite based X-ray detectors for dose monitoring in medical imaging applications. *Physics in Medicine* 5, 20-23 (2018).
16. Thirimanne, H. et al. High sensitivity organic inorganic hybrid X-ray detectors with direct transduction and broad-band response. *Nature communications* 9, 2926 (2018).
17. Wei, H. et al. Sensitive X-ray detectors made of methylammonium lead tribromide perovskite single crystals. *Nature Photonics* 10, 333 (2016).
18. Kasap, S. Low-cost X-ray detectors. *Nature Photonics* 9, 420, doi:10.1038/nphoton.2015.108 (2015).
19. Babu, R., Giribabu, L. & Singh, S. P. Recent Advances in Halide-Based Perovskite Crystals and Their Optoelectronic Applications. *Crystal Growth & Design* 18, 2645-2664 (2018).

Efforts have been made to ensure accuracy with respect to numbers used (e.g., amounts, temperature, etc.) but some experimental errors and deviations should be accounted for.

One skilled in the art will recognize many methods and materials similar or equivalent to those described herein, which could be used in the practicing the subject matter described herein. The present disclosure is in no way limited to just the methods and materials described.

Unless defined otherwise, technical and scientific terms used herein have the same meaning as commonly understood by one of ordinary skill in the art to which this subject matter belongs.

Throughout this specification and the claims, the words "comprise," "comprises," and "comprising" are used in a non-exclusive sense, except where the context requires otherwise. It is understood that embodiments described herein include "consisting of" and/or "consisting essentially of" embodiments.

Where a range of values is provided, it is understood that each intervening value, to the tenth of the unit of the lower limit, unless the context clearly dictates otherwise, between the upper and lower limit of the range and any other stated or intervening value in that stated range, is encompassed. The upper and lower limits of these small ranges which may independently be included in the smaller rangers is also encompassed, subject to any specifically excluded limit in the stated range. Where the stated range includes one or both of the limits, ranges excluding either or both of those included limits are also included.

Many modifications and other embodiments set forth herein will come to mind to one skilled in the art to which this subject matter pertains having the benefit of the teachings presented in the foregoing descriptions and the associated drawings. Therefore, it is to be understood that the subject matter is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A multilayer composite film, comprising two or more layers,
wherein, each layer comprises:
i. a porous membrane comprising interconnected channels; and
ii. a radiation sensitive material comprising a plurality of crystals,
wherein the plurality of crystals are embedded in the interconnected channels of said porous membrane;
wherein said porous membrane and said radiation sensitive material in each adjacent layer are the same or different to those of any other layer; and said multilayer composite film is continuous; and
wherein at least a portion of the interconnected channels of two adjacent layers of the multilayer composite film are connected.

2. The multilayer composite film of claim 1, wherein said crystals have a size of about 50 nanometers to about 500 micrometers.

3. The multilayer composite film of claim 1, wherein said radiation sensitive material comprising a plurality of crystals is selected from the group consisting of:
a. a perovskite having a formula of $ABX_3$, wherein A is a cation selected from the group consisting of methylammonium (MA), tetramethylammonium, formamidinium (FA), cesium, rubidium, potassium, sodium, butylammonium, phenethylammonium, phenylammonium, guanidinium, ammonium, and a combination thereof; B is a metal cation selected from the group consisting of lead, tin, cadmium, germanium, zinc, nickel, platinum, palladium, mercury, titanium, silicon, and a combination thereof; and X is a halide selected from the group consisting of $Cl^-$, $Br^-$, $F^-$, $I^-$, and a combination thereof;
b. a perovskite having a formula of $ABO_3$, wherein A is a cation selected from the group consisting of barium, magnesium, calcium, strontium, lanthanum, neodymium, praseodymium, cerium, samarium, europium, gadolinium, terbium, dysprosium, holmium, erbium, ytterbium, lutetium, and a combination thereof; B is a metal cation selected from the group consisting of silicon, titanium, iron, manganese, cobalt, nickel, aluminum, and a combination thereof; and O is oxygen;
c. a perovskite having a formula of $A_2B'B''X_6$, wherein A is a cation selected from the group consisting of methylammonium (MA), tetramethylammonium, formamidinium (FA), cesium, rubidium, potassium, sodium, butylammonium, phenethylammonium, phenylammonium, guanidinium, ammonium, and a combination thereof; B' and B'' are each independently a metal cation selected from the group consisting of lead, tin, cadmium, germanium, zinc, nickel, platinum, palladium, mercury, titanium, silicon, silver, copper, gold, calcium, bismuth, gallium, indium, antimony, and a combination thereof; and X is a halide selected from the group consisting of $Cl^-$, $Br^-$, $F^-$, $I^-$, and a combination thereof; and
d. a material selected from the group consisting of α-Se, CsI: Tl, $HgI_2$, $PbI_2$, $Gd_2O_2S$:Tb, Cd(Zn)Te, and $(NH_4)_3Bi_2I_9$.

4. The multilayer composite film of claim 3, wherein said radiation sensitive material comprising a plurality of crystals is a perovskite having the formula of $ABX_3$, wherein A is a cation selected from the group consisting of methylammonium (MA), tetramethylammonium, formamidinium (FA), cesium, rubidium, potassium, sodium, butylammonium, phenethylammonium, phenylammonium, guanidinium, ammonium, and a combination thereof; B is a metal cation selected from the group consisting of lead, tin, cadmium, germanium, zinc, nickel, platinum, palladium, mercury, titanium, silicon, and a combination thereof; and X is a halide selected from the group consisting of $Cl^-$, $Br^-$, $F^-$, $I^-$, and a combination thereof.

5. The multilayer composite film of claim 4, wherein said perovskite having the formula of $ABX_3$ is selected from the group consisting of $MAPbBr_3$, $MAPbI_3$, $MAPbCl_3$, and $MAPb(I_{0.9}Cl_{0.1})_3$.

6. The multilayer composite film of claim 1, wherein said composite film has a thickness of about 50 nm to about 1 cm.

7. The multilayer composite film of claim 1, wherein said composite film is smooth.

8. The multilayer composite film of claim 1, wherein said porous membrane comprises a material selected from the group consisting of metal, ceramic, polymer, carbon, protein, and a combination thereof.

9. The multilayer composite film of claim 8, wherein said polymer is selected from the group consisting of nylon, low-density polyethylene (LDPE), high-density polyethylene (HDPE), polypropylene (PP), polyvinyl chloride (PVC), polyvinylidene fluoride (PVDF), polystyrene (PS), polytetrafluoroethylene (PTFE), polyimide, polyamide, polyacrilonitrile (PAN), polysulfone (PS), polyether sulfone (PES), cellulose, cellulose acetate, methyl cellulose, ethyl cellulose, nitrocellulose, hydroxylpropylcellulose (HPC), hydroxyethylcellulose (HEC), carboxymethylcellulose (CMC), polycarbonate (PCTE), polyether ether ketone (PEEK), and polydimethylsiloxane (PDMS).

10. The multilayer composite film of claim 9, wherein said polymer is nylon.

11. The multilayer composite film of claim 8, wherein said ceramic is selected from the group consisting of alumina ($Al_2O_3$), titania ($TiO_2$), zirconium oxide ($ZrO_2$), silicon carbide (SiC), silicon dioxide ($SiO_2$), spinel ($MgAl_2O_4$), mullite selected from $3Al_2O_3$-$2SiO_2$ or $2Al_2O_3$—$SiO_2$, aluminum nitride (AlN), aluminum carbide ($Al_4C_3$), silicon nitride ($Si_3N_4$), silicon carbon nitride (SiCN), silicon aluminum carbon nitride (SiAlCN), zinc oxide (ZnO), Barium titanate ($BaTiO_3$), boron oxide, boron nitride, zirconium nitride (ZrN), titanium carbide (TiC), titanium nitride (TiN), and a combination thereof.

12. The multilayer composite film of claim 8, wherein said metal is selected from the group consisting of Pd, Ag, Cu, Fe, Ni, W, Ti, Mo, Zn, Pt, Sn, Pb, Ga, Mg, Bi, Al, and stainless steel.

13. The multilayer composite film of claim 8, wherein said carbon is selected from the group consisting of carbon nanotubes (CNTs), carbon nanofibers (CNFs), carbon fiber, graphene, carbon nanohorns (CNHs), and carbon nanoparticles (CNPs).

14. The multilayer composite film of claim 1, wherein said composite film is flexible.

15. An X-ray device comprising the multilayer composite film of claim 1, and an electrode.

16. An X-ray detector comprising the multilayer composite film of claim 1, an optional first transport layer, a second transport layer, a first electrode, and a second electrode, wherein said first transport layer, if present, is disposed on said first electrode, said composite film is disposed on said first transport layer if present, said second transport layer is disposed on said composite film, and said second electrode is disposed on said second transport layer.

17. A method of preparing a multilayer continuous composite film comprising two or more layers, said method comprising:
   a) passing a radiation sensitive material precursor solution through a porous membrane comprising interconnected channels, wherein one or more crystals of the radiation sensitive material are retained in the interconnected channels of said porous membrane;
   wherein a) is carried out two or more times to prepare said two or more layers; wherein said radiation sensitive material precursor solution and said porous membrane in adjacent layers are the same or different; and
   b) compressing said two or more layers to prepare said continuous composite film,
   wherein at least a portion of the interconnected channels of two adjacent layers of said continuous composite film are connected.

* * * * *

UNITED STATES PATENT AND TRADEMARK OFFICE
CERTIFICATE OF CORRECTION

| | | |
|---|---|---|
| PATENT NO. | : 12,372,672 B2 | Page 1 of 1 |
| APPLICATION NO. | : 17/769067 | |
| DATED | : July 29, 2025 | |
| INVENTOR(S) | : Jinsong Huang et al. | |

It is certified that error appears in the above-identified patent and that said Letters Patent is hereby corrected as shown below:

In the Claims

In Column 33, Line 66, Claim 3, delete "CsI: TI, HgI$_2$," and insert -- CsI:TI, HgI$_2$, --, therefor.

In Column 34, Line 45, Claim 11, delete "2Al$_2$O$_3$—SiO$_2$," and insert -- 2Al$_2$O$_3$-SiO$_2$, --, therefor.

Signed and Sealed this
Twentieth Day of January, 2026

John A. Squires
*Director of the United States Patent and Trademark Office*